US008034464B2

(12) United States Patent
Igawa et al.

(10) Patent No.: US 8,034,464 B2
(45) Date of Patent: Oct. 11, 2011

(54) FLUORENE DERIVATIVE AND ORGANIC ELECTROLUMINESCENCE DEVICE USING THE SAME

(75) Inventors: Satoshi Igawa, Fujisawa (JP); Shinjiro Okada, Kamakura (JP); Takao Takiguchi, Tokyo (JP); Masashi Hashimoto, Tokyo (JP); Naoki Yamada, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 683 days.

(21) Appl. No.: 11/686,002

(22) Filed: Mar. 14, 2007

(65) Prior Publication Data

US 2007/0232841 A1 Oct. 4, 2007

(30) Foreign Application Priority Data

Mar. 31, 2006 (JP) ................................ 2006-099895

(51) Int. Cl.
*H01L 51/54* (2006.01)
(52) U.S. Cl. ........ 428/690; 428/917; 313/504; 313/505; 313/506; 585/27
(58) Field of Classification Search .................. 428/690, 428/917; 313/504, 505, 506; 585/27
See application file for complete search history.

(56) References Cited

U.S. PATENT DOCUMENTS

| 7,241,513 B2 | 7/2007 | Suzuki et al. | 428/690 |
|---|---|---|---|
| 2004/0253389 A1 | 12/2004 | Suzuki et al. | 428/1.1 |
| 2005/0148460 A1* | 7/2005 | Marin et al. | 502/152 |
| 2005/0236974 A1 | 10/2005 | Suzuki et al. | 313/504 |
| 2006/0003171 A1* | 1/2006 | Igawa et al. | 428/447 |
| 2006/0121312 A1 | 6/2006 | Yamada et al. | 428/690 |
| 2006/0166034 A1 | 7/2006 | Saitoh et al. | 428/690 |
| 2007/0111029 A1 | 5/2007 | Yamada et al. | 428/690 |
| 2007/0122652 A1 | 5/2007 | Hashimoto et al. | 428/690 |
| 2007/0184302 A1 | 8/2007 | Iwawaki et al. | 428/690 |

FOREIGN PATENT DOCUMENTS

| JP | 2003-142267 | 5/2003 |
|---|---|---|
| JP | 2003-261471 | 9/2003 |
| JP | 2004-273128 | 9/2004 |

OTHER PUBLICATIONS

Kauffman, J of Fluorescene, vol. 5, No. 3, 1995, p. 295-305.*
Surin, Correlation . . . Fluorene-Based Polymers and Copolymers, 2004, Chemical Materials, 16, p. 994-1001.*
Larock et. al., Synthesis of Fused Polycycles . . . , 2004, J. Org. Chem., vol. 69, pp. 8251-8257.*
Burroughes et al., "Light-emitting Diodes Based on Conjugated Polymers," *Nature*, vol. 347, 539-541 (1990).
Vincett et al., "Electrical Conduction and Low Voltage Blue Electroluminescence in Vacuum-Deposited Organic Films," *Thin Solid Films*, vol. 94, 171-183 (1982).
Chen et al., Recent Developments in Molecular Organic Electroluminescent Materials, *Macromol. Symp.* vol. 125, 1-48 (1997).
O'Brien et al., "Improved Energy Transfer in Electrophosphorescent Devices," *App. Phys. Lett.*, vol. 74, No. 3, 442-444 (1999).
Baldo et al., "Very High-efficiency Green Organic Light-emitting Devices Based on Electrophosphorescence," *App. Phys. Lett.*, vol. 75, No. 1, 4-6 (1999).

* cited by examiner

*Primary Examiner* — D. Lawrence Tarazano
*Assistant Examiner* — Gregory Clark
(74) *Attorney, Agent, or Firm* — Fitzpatrick, Cella, Harper & Scinto

(57) ABSTRACT

A fluorene derivative represented by the following structural formula. An organic electroluminescence device including a pair of electrodes, and at least one layer containing an organic compound interposed between the pair of the electrodes. The at least one layer containing the organic compound contains the fluorene derivative. The layer containing the fluorene derivative serves as a light-emitting layer.

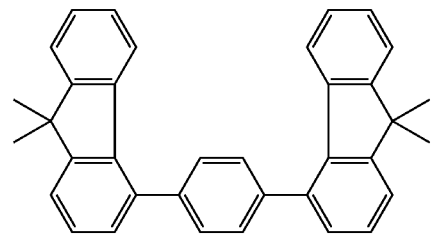

16 Claims, 2 Drawing Sheets

FLUORENE DERIVATIVE AND ORGANIC ELECTROLUMINESCENCE DEVICE USING THE SAME

BACKGROUND OF THE INVENTION

1. Field of the Invention

The present invention relates to a fluorene derivative, and to an organic electroluminescence device (hereinafter, sometimes referred to as "organic EL device") using the same. In particular, the present invention relates to an organic EL device having highly stable emission efficiency, which is obtained by using a fluorene derivative as a host in a light-emitting layer.

2. Description of the Related Art

In an old example of an organic EL device, a voltage has been applied to an anthracene evaporated film to emit light (see, Thin Solid Films, 94 (1982), 171). In recent years, however, applied research has been vigorously conducted on a transformation of an organic EL device as a light-emitting device having high-speed response and high efficiency into a device, including developments of materials for the device. This is because the device has such advantages that an area of the organic EL device can be increased more easily than that of an inorganic light-emitting device, the device provides desired color development through the developments of various new materials, and the device can be driven at a low voltage.

For example, as described in Macromol. Symp. 125, 1 to 48 (1997), an organic EL device generally includes a transparent substrate, two upper and lower electrodes formed on the transparent substrate, and an organic material layer including a light-emitting layer, the organic material layer being interposed between the two electrodes.

In recent years, investigation has been made into a device utilizing not only conventional light emission utilizing fluorescence upon transition from an excited singlet state to a ground state but also phosphorescence via a triplet exciton which is represented by technologies described in each of "Improved energy transfer in electrophosphoresent device", D. F. O'Brien et al., Applied Physics Letters, Vol 74, No 3, p 422 (1999) and "Very high-efficiency green organic light-emitting devices based on electrophosphorescence", M. A. Baldo et al., Applied Physics Letters, Vol 75, No 1, p 4 (1999). In each of those documents, an organic layer having a four-layer structure has been mainly used. The organic layer includes a hole-transporting layer, a light-emitting layer, an exciton diffusion-prevention layer, and an electron-transporting layer from an anode side. Materials used are a carrier-transporting material and a phosphorescent material $Ir(ppy)_3$ shown below.

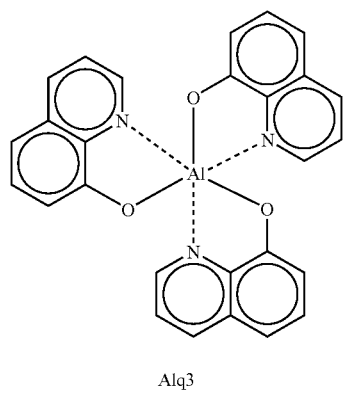

Alq3

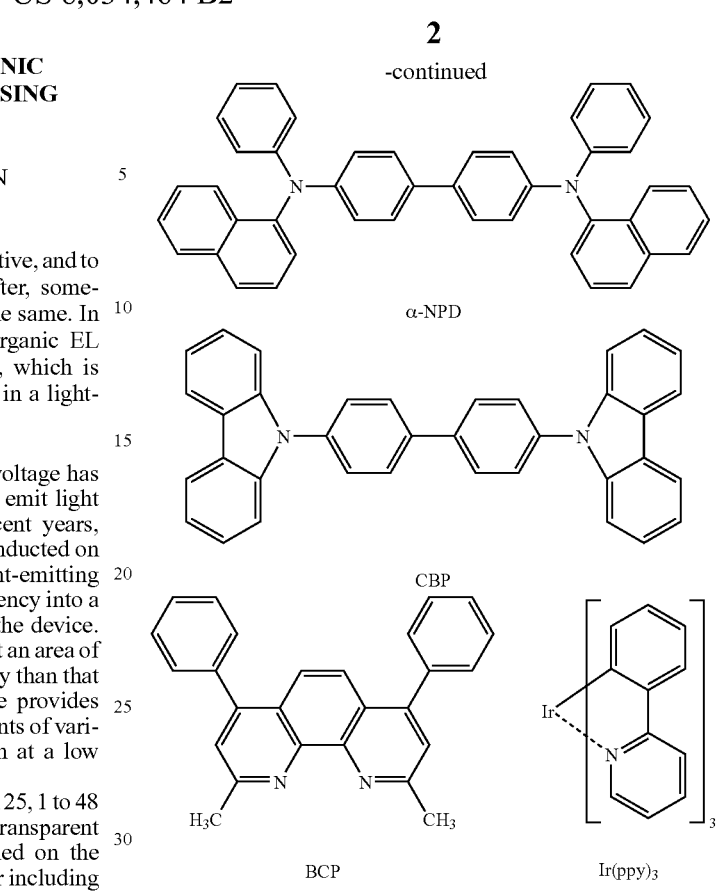

α-NPD

CBP

BCP

Ir(ppy)₃

Further, as host materials of a triplet luminescent material typified by those described in Japanese Patent Application Laid-Open No. 2003-142267 and Japanese Patent Application Laid-Open No. 2004-273128, developments of host materials having high lowest excited triplet states (T1) have been conducted.

A variety of light ranging from ultraviolet light to infrared light can be emitted by changing the kind of a fluorescent organic compound. In recent years, active research has been conducted on various compounds.

In addition to an organic light-emitting device using any one of the low-molecular-weight materials as described above, an organic light-emitting device using a conjugate polymer has been reported by the group of the University of Cambridge (see, Nature, 347, 539 (1990)). In this report, there has been observed light emission from a single layer by forming polyphenylenevinylene (PPV) into a film by means of a coating system.

As described above, an organic light-emitting device has recently showed significant progress. The organic light-emitting device is characterized in that the organic light-emitting device can be transformed into a high-speed response, thin, and lightweight light-emitting device which can be driven at a low applied voltage and has high luminance and a variety of emission wavelengths. The characteristic suggests the potential of the device to find use in a wide variety of applications.

However, at present, output of light having additionally higher luminance, or additionally higher conversion efficiency is required. In addition, there still remain a large number of problems in terms of durability such as a change with time due to long-term use and deterioration due to an atmospheric gas containing oxygen or due to moisture. Further, although luminescence of blue, green, and red which have good color purity are necessary when the organic light-emitting device is applied to a full-color display and the like, the light-emitting device has not overcome the problem.

In addition, a large number of aromatic compounds and condensed polycyclic aromatic compounds have been investigated for their potential as a fluorescent organic compound to be used in an electron-transporting layer, a light-emitting layer, and the like. However, there is not yielded one which has sufficient luminance and durability.

Japanese Patent Application Laid-Open No. 2003-261471 describes application of a compound having a substituent at a position 4 of fluorene, which is related to the present invention, to an organic EL device.

SUMMARY OF THE INVENTION

Japanese Patent Application Laid-Open No. 2003-261471 as mentioned above discloses application of a compound having a substituent at a position 4 of fluorene to an organic EL device, but does not disclose a fluorene derivative of the present invention, which has a hydrocarbon skeleton composed of fluorene and a phenylene group which are bonded to each other at the position 4 of the fluorene.

In order to apply an organic EL device to a display apparatus such as a display, it is necessary to ensure output of light with high luminance and high efficiency, and high durability at the same time. However, the organic EL device has not overcome the problem.

The present invention has been made in view of the above-mentioned background art. Thus, it is an object of the present invention to provide, as a compound for an organic EL device, a fluorene derivative having a particular structure, and an organic EL device which outputs light with high luminance and high efficiency and which is obtained by using the fluorene derivative.

In addition, the present invention is also intended to provide: an organic EL device with high durability; and an organic EL device which can be easily produced at low cost.

(1) According to an aspect of the present invention, there is provided a fluorene derivative, which is represented by the general formula (I):

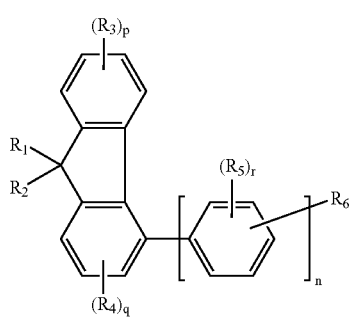

where, $R_1$ and $R_2$ each represent a hydrogen atom, an alkyl group, a substituted or unsubstituted aralkyl group, a substituted or unsubstituted aryl group, or a substituted or unsubstituted heterocyclic group, provided that $R_1$ and $R_2$ may be identical to or different from each other;

$R_3$ and $R_4$ each represent a linear, branched, or cyclic alkyl group wherein at least one methylene group in the alkyl group may be substituted by —O—, —S—, —CO—, —CO—O—, —O—CO—, —CH=CH—, —C≡C—, or an arylene group which may have a substituent, and a hydrogen atom in the alkyl group may be substituted by a fluorine atom; a substituted or unsubstituted aryl group; or a halogen atom, provided that, when $R_3$ and $R_4$ are each present in plurality, $R_3$'s may be identical to or different from each other, and $R_4$'s may be identical to or different from each other;

p represents an integer of 0 to 4, and q represents an integer of 0 to 3;

$R_5$ represents a linear, branched, or cyclic alkyl group wherein at least one methylene group in the alkyl group may be substituted by —O—, —S—, —CO—, —CO—O—, —O—CO—, —CH=CH—, —C≡C—, or an arylene group which may have a substituent, and a hydrogen atom in the alkyl group may be substituted by a fluorine atom; a halogen atom; or a substituted or unsubstituted aryl group, provided that, when $R_5$ is present in plurality, $R_5$'s may be identical to or different from each other;

r represents an integer of 0 to 4;

when the phenylene group is present in plurality, the substituents $R_5$'s of phenylene groups may be identical to or different from each other, and the substituents $R_6$'s of phenylene groups may be identical to or different from each other;

n represents an integer of 1 to 10; and $R_6$ represents a hydrogen atom, a substituted or unsubstituted aryl group, or a linear, branched, or cyclic alkyl group.

(2) According to another aspect of the present invention, in the fluorene derivative according to the above-mentioned item (1), $R_6$ in the general formula (I) is represented by the general formula (II):

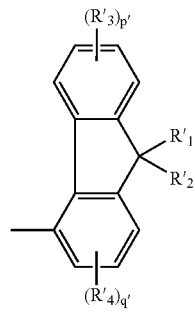

where, $R'_1$ and $R'_2$ each represent a hydrogen atom, an alkyl group, a substituted or unsubstituted aralkyl group, a substituted or unsubstituted aryl group, or a substituted or unsubstituted heterocyclic group, provided that $R'_1$ and $R'_2$ may be identical to or different from each other;

$R'_3$ and $R'_4$ each represent a linear, branched, or cyclic alkyl group wherein at least one methylene group in the alkyl group may be substituted by —O—, —S—, —CO—, —CO—O—, —O—CO—, —CH=CH—, —C≡C—, or an arylene group which may have a substituent, and a hydrogen atom in the alkyl group may be substituted by a fluorine atom; a substituted or unsubstituted aryl group; or a halogen atom, provided that, when $R'_3$ and $R'_4$ are each present in plurality, $R'_3$'s may be identical to or different from each other, and $R'_4$'s may be identical to or different from each other; and p' represents an integer of 0 to 4, and q' represents an integer of 0 to 3.

(3) According to another aspect of the present invention, in the fluorene derivative according to the above-mentioned item (1), $R_6$ in the general formula (I) is a hydrogen atom, or a linear, branched, or cyclic alkyl group.

(4) According to another aspect of the present invention, there is provided an organic electroluminescence device, including:

a pair of electrodes; and an organic compound layer which is interposed between the pair of the electrodes, in which the organic compound layer includes the fluorene derivative according to the above-mentioned item (1).

(5) According to another aspect of the present invention, in the organic electroluminescence device according to the above-mentioned item (4), the organic compound layer is a light-emitting layer.

(6) According to another aspect of the present invention, in the organic electroluminescence device according to the above-mentioned item (5), the light-emitting device at least includes two compounds which are a host and a guest, respectively.

(7) According to another aspect of the present invention, in the organic electroluminescence device according to the above-mentioned item (6), the host is the fluorene derivative according to the above-mentioned item (1).

(8) According to another aspect of the present invention, in the organic electroluminescence device according to the above-mentioned item (6), the guest is a phosphorescent material.

(9) According to another aspect of the present invention, in the organic electroluminescence device according to the above-mentioned item (8), the phosphorescent material is a metal coordination compound.

(10) According to another aspect of the present invention, in the organic electroluminescence device according to the above-mentioned item (9), the metal coordination compound is an iridium coordination compound.

The organic EL device using as a host in a light-emitting layer the fluorene derivative of the present invention can emit light with high efficiency and retain high luminance for a long period of time.

Further features of the present invention will become apparent from the following description of exemplary embodiments with reference to the attached drawings.

DESCRIPTION OF THE EMBODIMENTS

Figure 1:
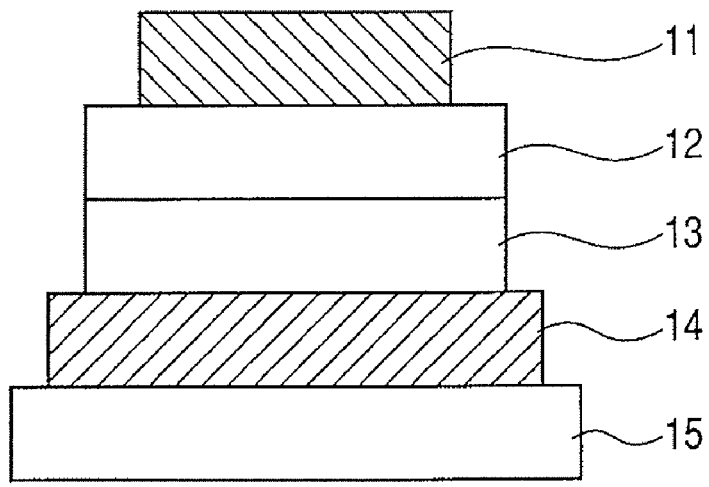
FIG. 1 shows an example of an organic EL device of the present invention.

Hereinafter, the present invention will be described in detail.

In a case where a light-emitting layer constituted by a host material having carrier-transporting property and a guest, main processes of luminescence includes the following:
1. transfer of electrons and holes in the light-emitting layer;
2. generation of excitons from the host;
3. transfer of excitation energy among molecules of the host; and
4. transfer of the excitation energy from the host to the guest.

Desired energy transfer and luminescence in respective processes occur owing to various deactivation processes and competitions.

In order to increase the emission efficiency of an organic EL device, it is necessary that the main luminescent material itself provide a large yield of luminescence quantum. However, it is a large problem that how efficiently the energy can be transferred between hosts, or between a host and a guest. In addition, although the reason why luminescence deterioration is caused by energization is not made clear at present, the luminescence deterioration is thought to be caused by change in environment of at least the main luminescence material or change in environment of the luminescence material caused by surrounding molecules.

Therefore, the inventors of the present invention have conducted various investigations, and have found that an organic EL device obtained by using as a host in a light-emitting layer a fluorene derivative represented by the general formula (I) emits light with high efficiency and retains high luminance for a long period of time with less deterioration due to energization.

The fluorene derivative of the present invention is represented by the general formula (I):

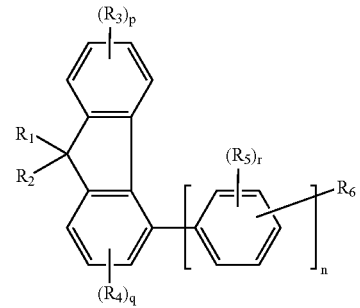

[I]

where, $R_1$ and $R_2$ each represent a hydrogen atom, an alkyl group, a substituted or unsubstituted aralkyl group, a substituted or unsubstituted aryl group, or a substituted or unsubstituted heterocyclic group.

Specifically, $R_1$ and $R_2$ are each selected from the group consisting of: a hydrogen atom; alkyl groups such as a methyl group, an ethyl group, a normal-propyl group, an isopropyl group, a normal-butyl group, a tertiary-butyl group, a hexyl group, an octyl group, a cyclohexyl group, and a trifluoromethyl group; aralkyl groups such as a benzyl group; aryl groups such as a phenyl group and naphthyl group; and heterocyclic groups such as pyridyl group. $R_1$ and $R_2$ each preferably represent an alkyl group from the viewpoint of stability to a radical of a carbon atom at a position 9 of the fluorenyl group. In addition, $R_1$ and $R_2$ each more preferably represent an alkyl group having a shorter carbon chain such as a methyl group and ethyl group because a glass transition temperature may decrease when $R_1$ and $R_2$ each represent a longer alkyl chain. In addition, $R_1$ and $R_2$ may be identical to or different from each other. However, $R_1$ and $R_2$ are preferably the same from the viewpoint of ease with synthesis.

$R_3$ and $R_4$ each represent a linear, branched, or cyclic alkyl group, in which at least one methylene group in the alkyl may be substituted by —O—, —S—; —CO—, —CO—O—, —O—CO—, —CH═CH—, —C≡C—, and an arylene group which may have a substituent, and a hydrogen atom in the alkyl group may be substituted by a fluorine atom; a substituted or unsubstituted aryl group; or a halogen atom. When $R_3$ and $R_4$ are each present in plurality, $R_3$'s may be identical to or different from each other, and $R_4$'s may be identical to or different from each other.

Specifically, $R_3$ and $R_4$ are each selected from the group consisting of: a hydrogen atom; alkyl groups such as a methyl group, an ethyl group, a normal-propyl group, an isopropyl group, a normal-butyl group, a tertiary-butyl group, an octyl group, a cyclohexyl group, and a trifluoromethyl group; aryl groups such as a phenyl group, a naphthyl group, and a tolyl group; and halogen atoms such as a fluorine atom, a chlorine atom, and a bromine atom.

p represents an integer of 0 to 4, and q represents an integer of 0 to 3.

$R_5$ represents a linear, branched, or cyclic alkyl group, in which at least one methylene group in the alkyl group may be substituted by —O—, —S—, —CO—, —CO—O—, —O—CO—, —CH═CH—, —C≡C—, and an arylene group which may have a substituent, and a hydrogen atom in the alkyl group may be substituted by a fluorine atom; a halogen atom; or a substituted or unsubstituted aryl group.

When $R_5$ is present in plurality, $R_5$'s may be identical to or different from each other.

Specifically, the substituent represented by $R_5$ is selected from the group consisting of: a hydrogen atom; alkyl groups such as a methyl group, an ethyl group, a normal-propyl group, an isopropyl group, a normal-butyl group, a tertiary-butyl group, an octyl group, a cyclohexyl group, and a trifluoromethyl group; halogen atoms such as a fluorine atom, a chlorine atom, and a bromine atom; and aryl groups such as a phenyl group, a naphthyl group, and a tolyl group.

r represents an integer of 0 to 4. When the phenylene group is present in plurality, the substituents $R_5$'s of phenylene groups may be identical to or different from each other, and the substituents $R_6$'s of phenylene groups may be identical to or different from each other.

n represents an integer of 1 to 10.

$R_6$ represents a hydrogen atom, a substituted or unsubstituted aryl group, or a linear, branched or cyclic alkyl group.

Specific examples of the substituent represented by $R_5$ include a phenyl group which may have a substituent, a naphthyl group, and fluorenyl group.

In addition, $R_6$ preferably represents a substituent represented by the general formula (II):

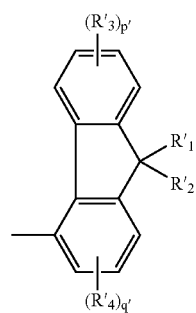

[II]

where, $R'_1$ and $R'_2$ each represent a hydrogen atom, an alkyl group, a substituted or unsubstituted aralkyl group, a substituted or unsubstituted aryl group, or a substituted or unsubstituted heterocyclic group, provided that $R'_1$ and $R'_2$ may be identical to or different from each other;

$R'_3$ and $R'_4$ each represent a linear, branched, or cyclic alkyl group wherein at least one methylene group in the alkyl group may be substituted by any one of —O—, —S—, —CO—, —CO—O—, —O—CO—, —CH=CH—, —C≡C—, or an arylene group which may have a substituent, and a hydrogen atom in the alkyl group may be substituted by a fluorine atom; a substituted or unsubstituted aryl group; or a halogen atom, provided that, when $R'_3$ and $R'_4$ are each present in plurality, $R'_3$'s may be identical to or different from each other, and $R'_4$'s may be identical to or different from each other; and p' represents an integer of 0 to 4, and q' represents an integer of 0 to 3.

In addition, $R_6$ may represent a hydrogen atom, or a linear, branched, or cyclic alkyl group.

The fluorene derivative of the present invention is a compound having a substituent at the 4-position of fluorene, so the fluorene derivative of the present invention has steric hindrance against a phenylene group bonded thereto, whereby high T1 level can be expected.

Hereinafter, structural formulae of the fluorene derivative of the present invention to be used in the present invention are specifically described. Note that, these structural formulae only show representative examples, and the present invention is not limited thereto.

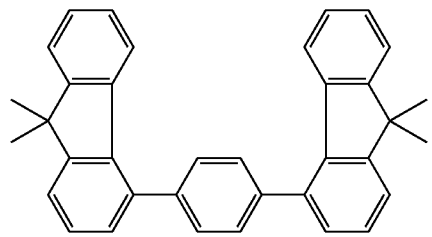

A-1

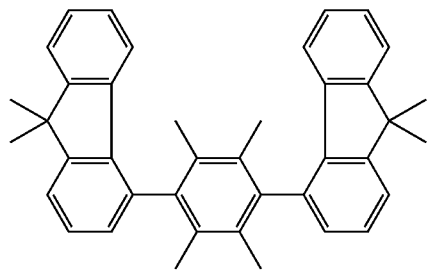

A-2

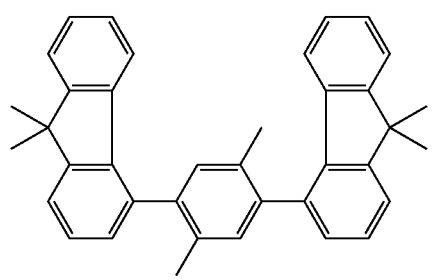

A-3

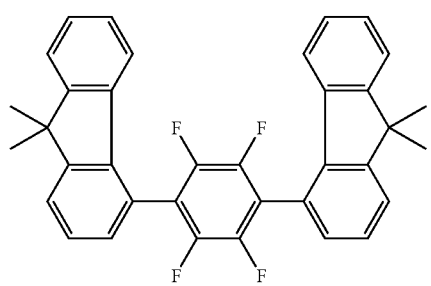

A-4

-continued
A-5
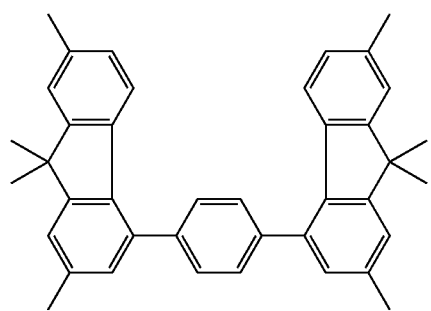
A-6
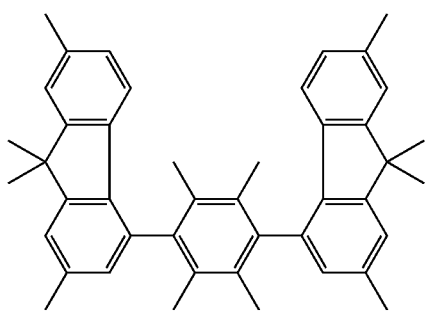
A-7
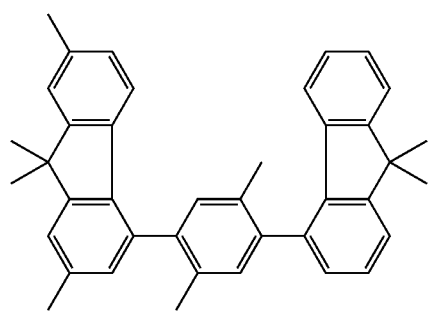
A-8
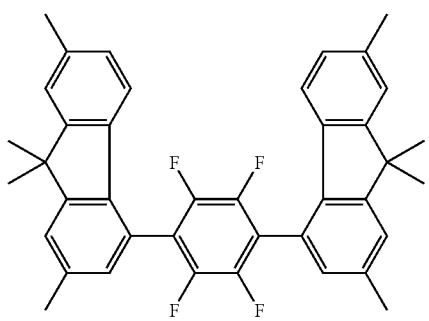
A-9
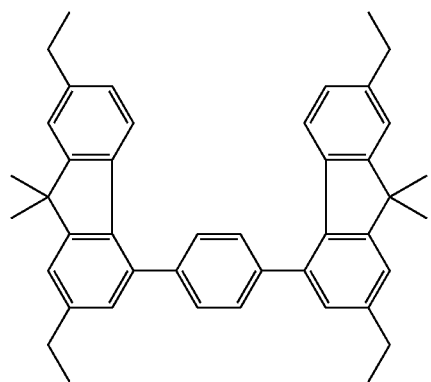
A-10
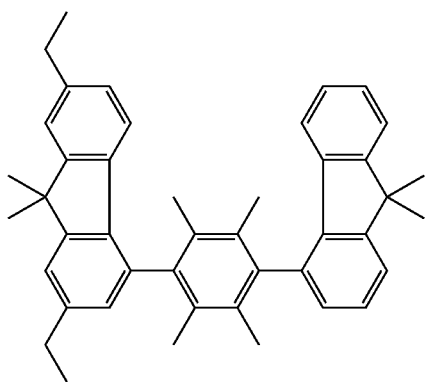
A-11
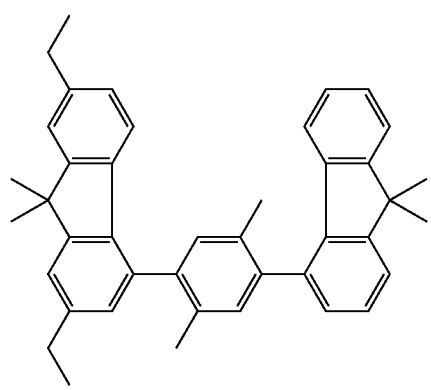
A-12
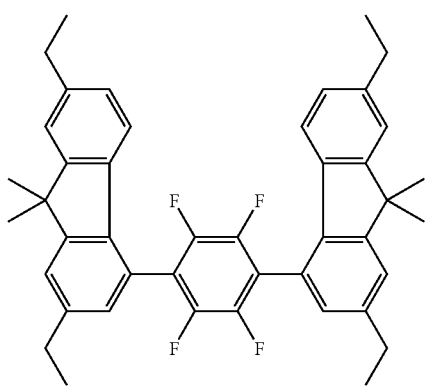

-continued
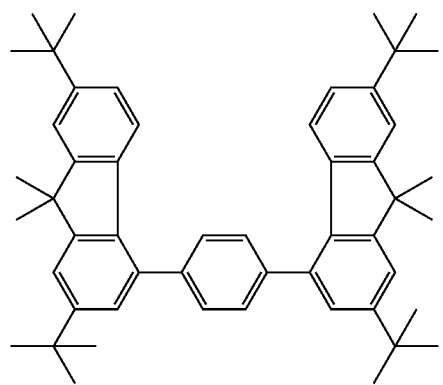
A-13
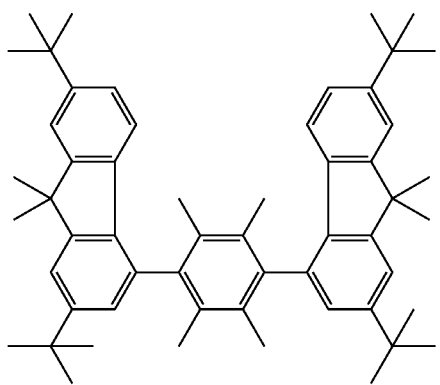
A-14
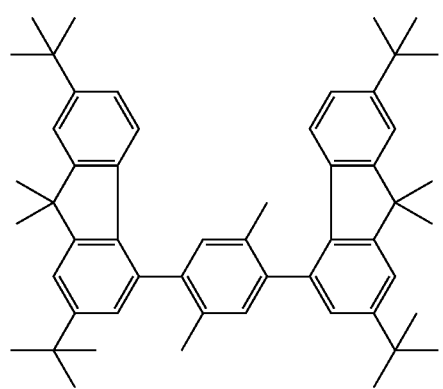
A-15
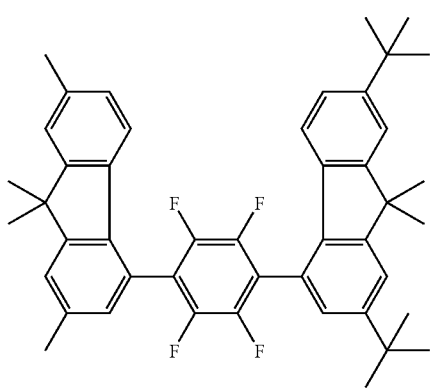
A-16
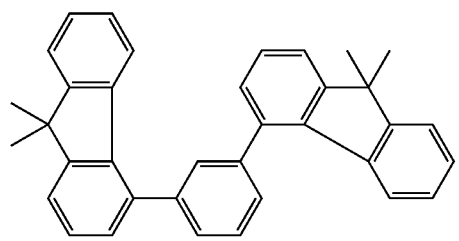
A-17
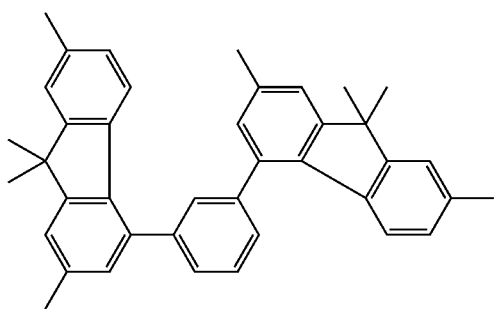
A-18
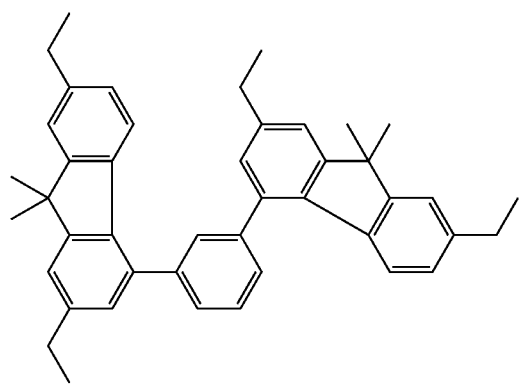
A-19
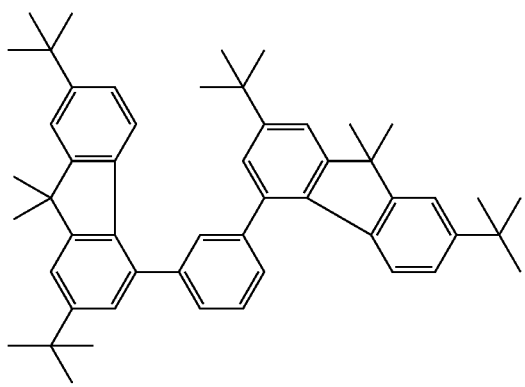
A-20

-continued
A-21
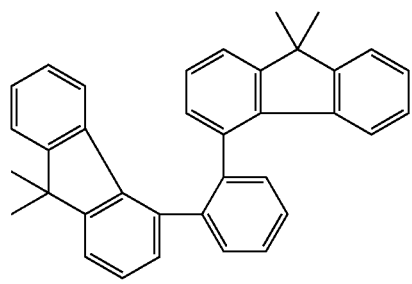
A-22
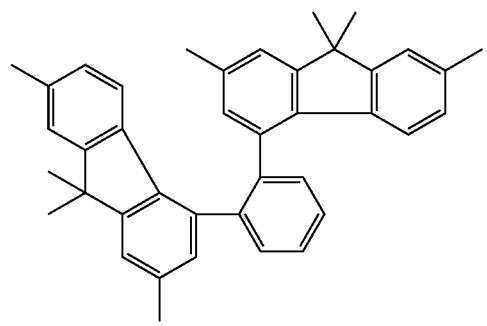
A-23
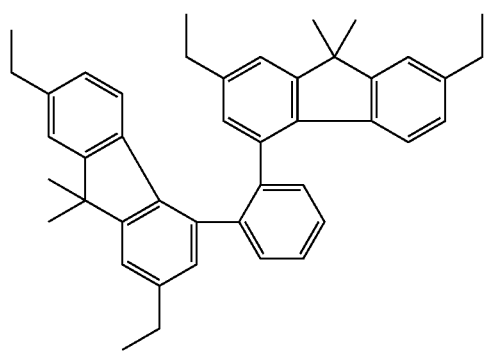
A-24
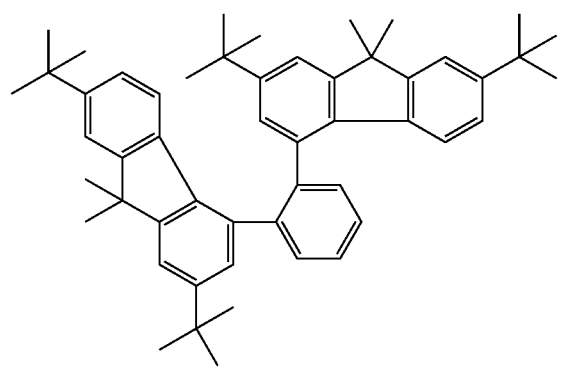
A-22-1
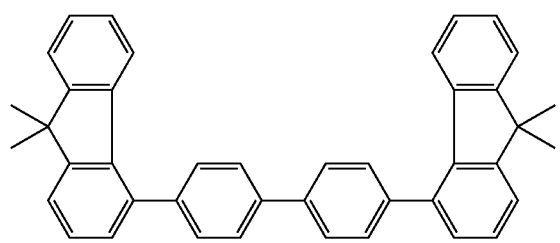
A-23-1
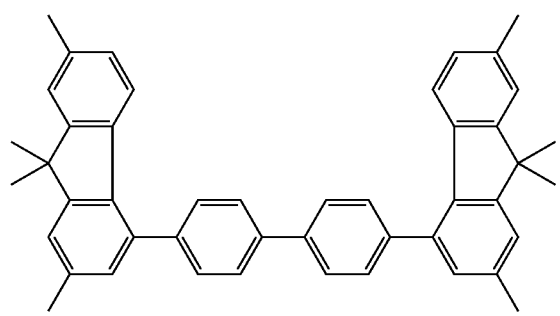
A-24-1
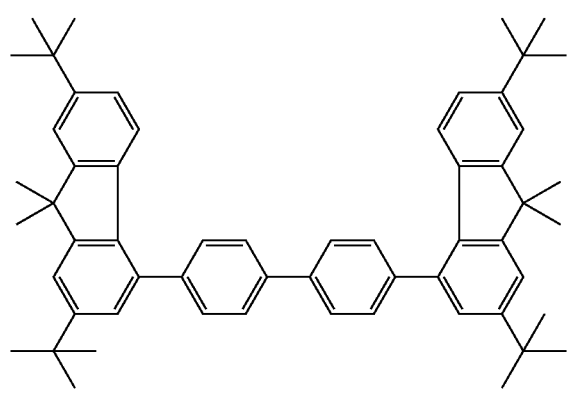
A-25
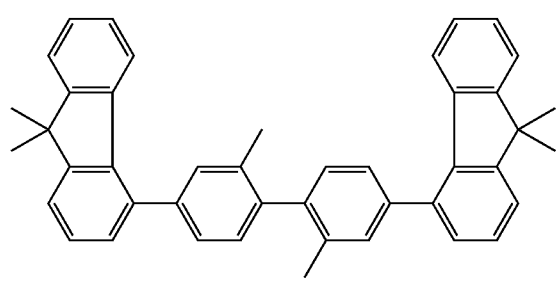

-continued
A-26
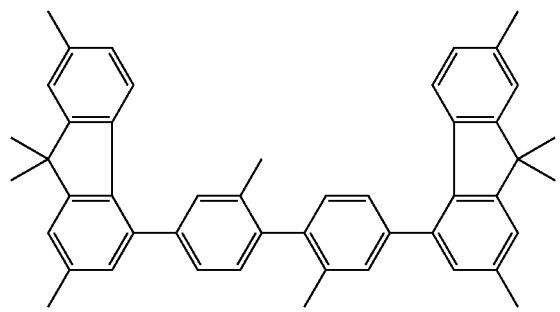
A-27
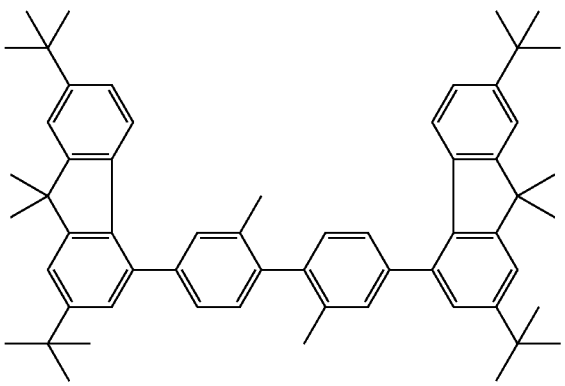
A-28
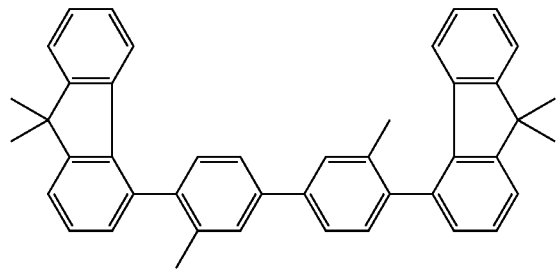
A-29
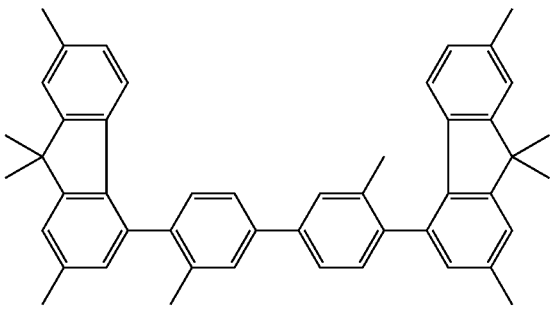
A-30
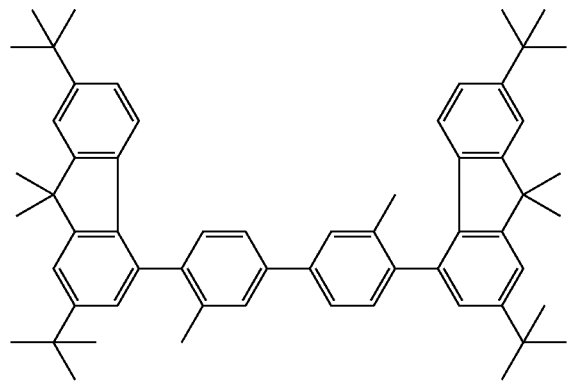
A-31
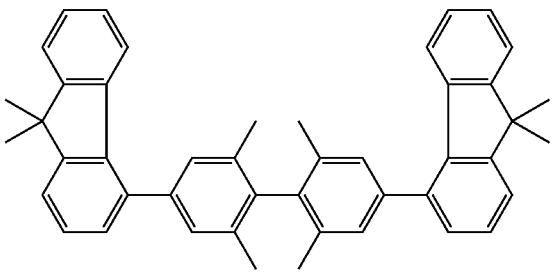
A-32
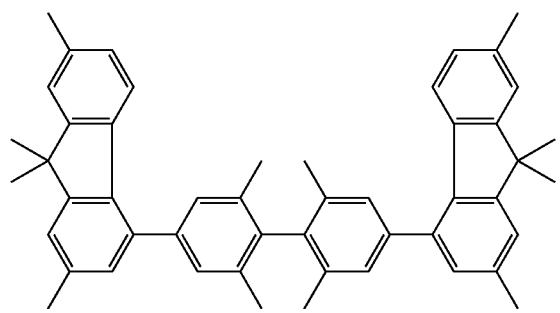
A-33
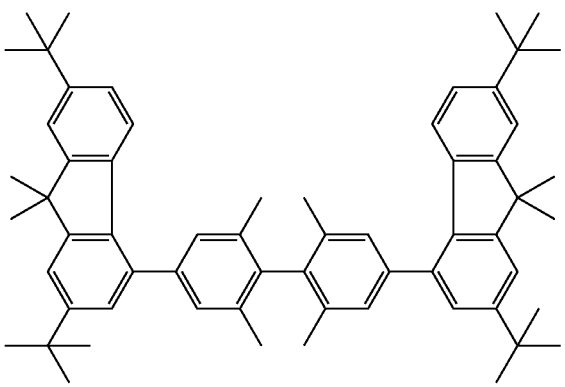

-continued
A-34
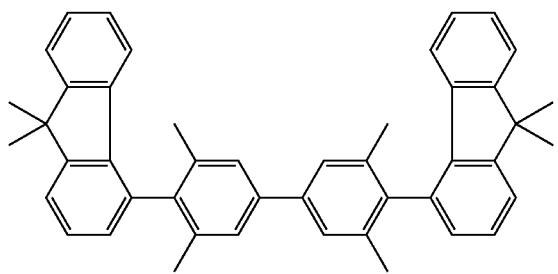
A-35
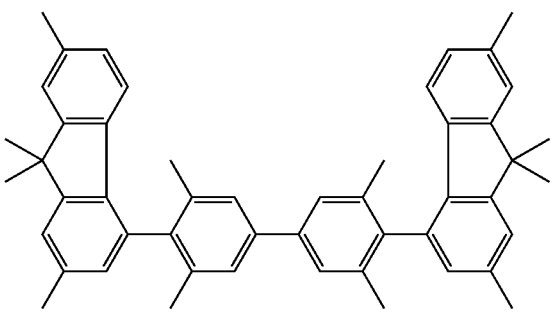
A-36
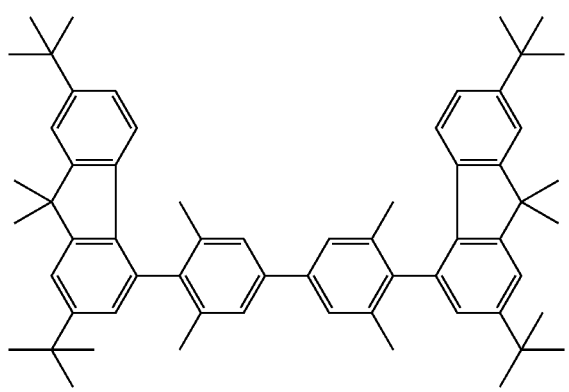
A-37
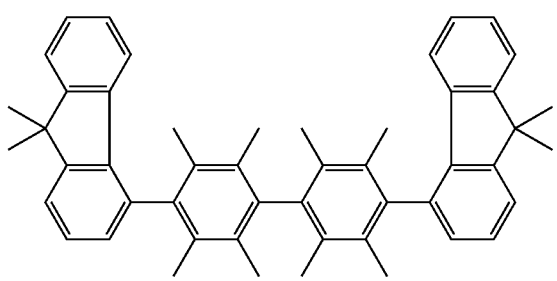
A-38
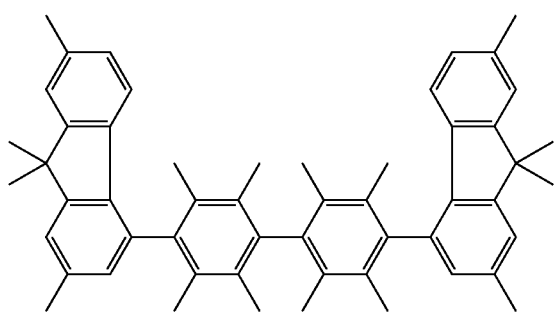
A-39
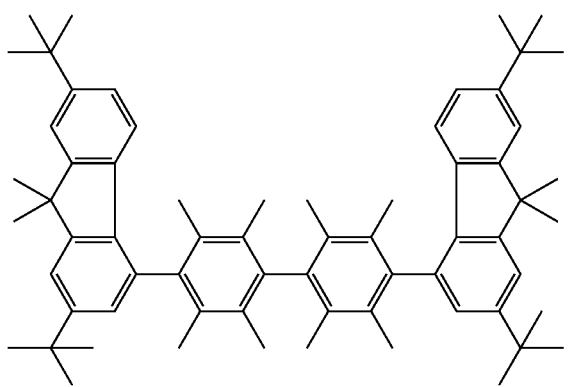
A-40
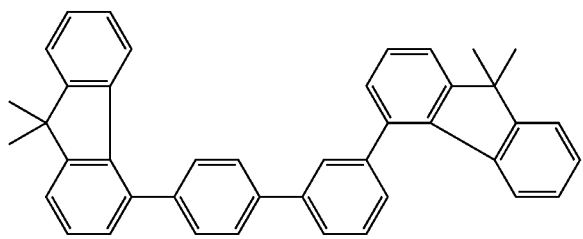

-continued
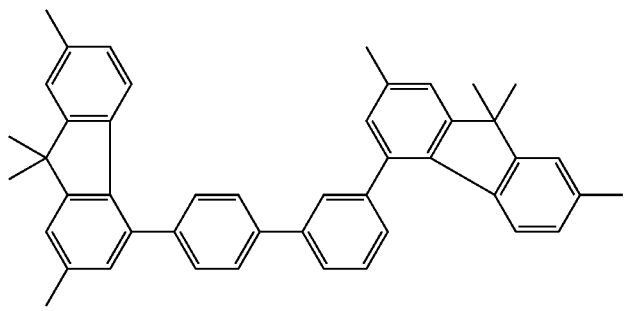
A-41
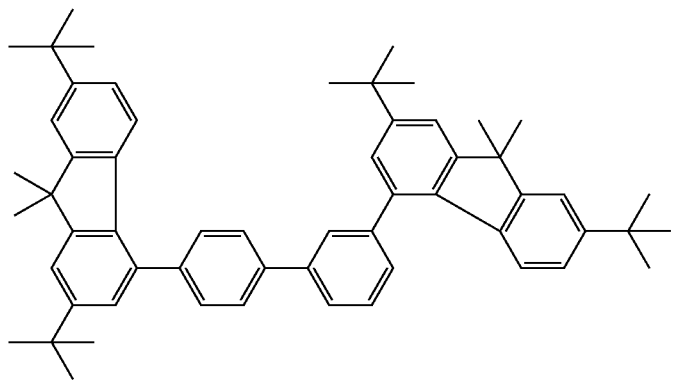
A-42
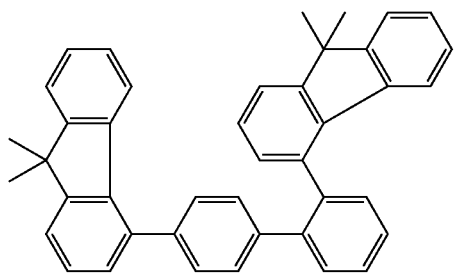
A-43
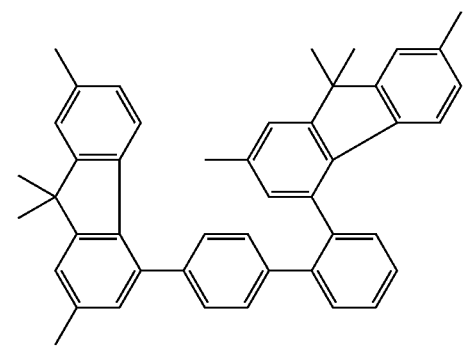
A-44
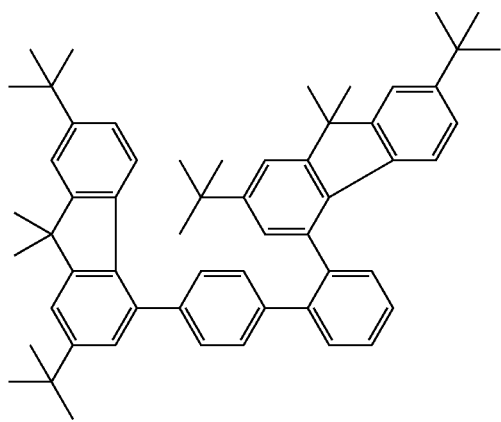
A-45
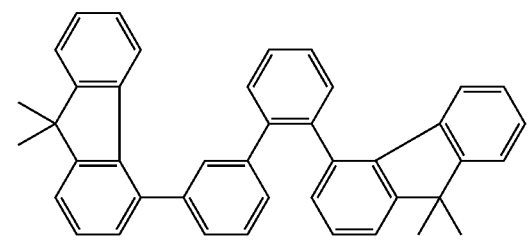
A-46

-continued
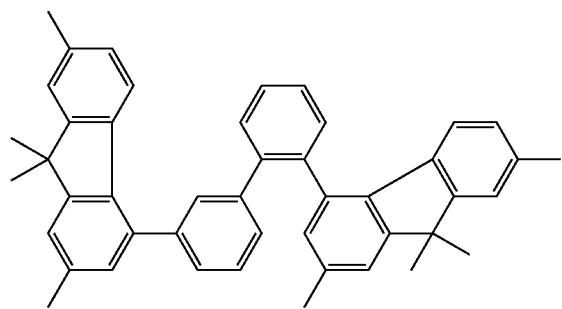
A-47
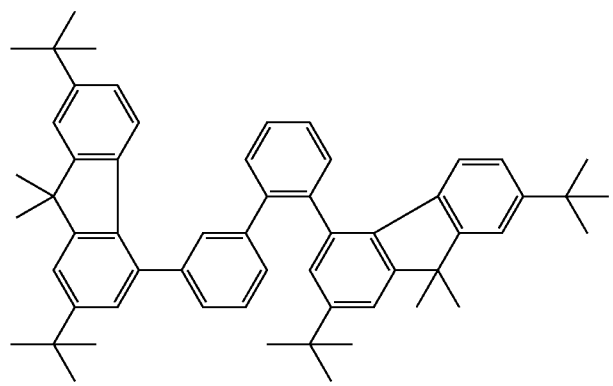
A-48
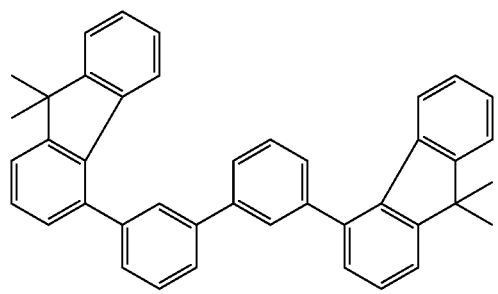
A-49
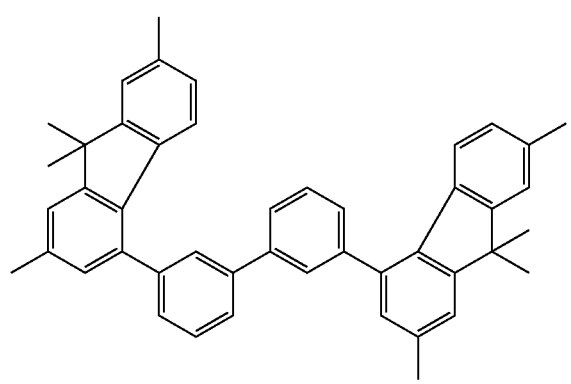
A-50

A-51
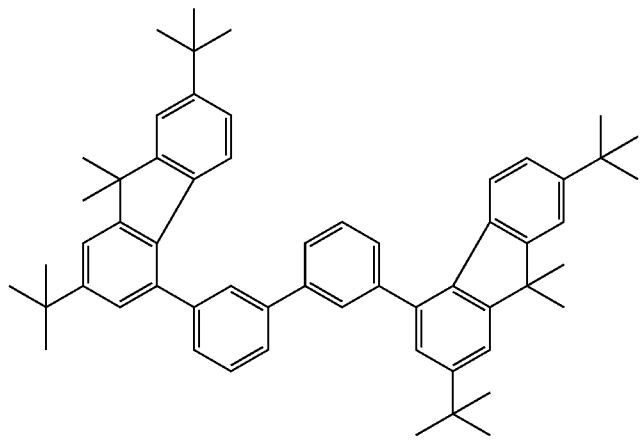
A-52
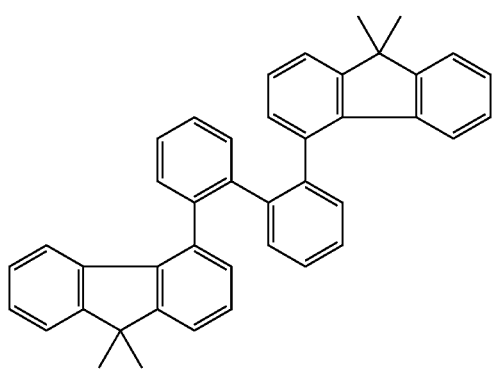
A-53
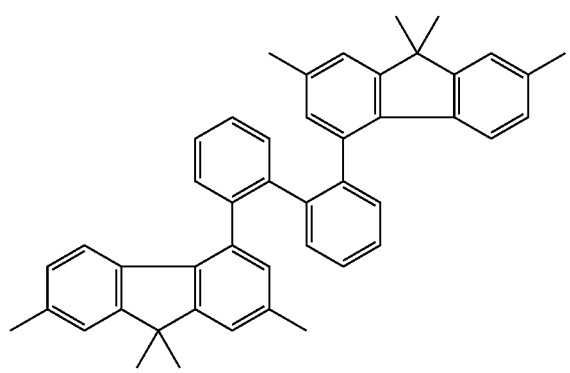
A-54
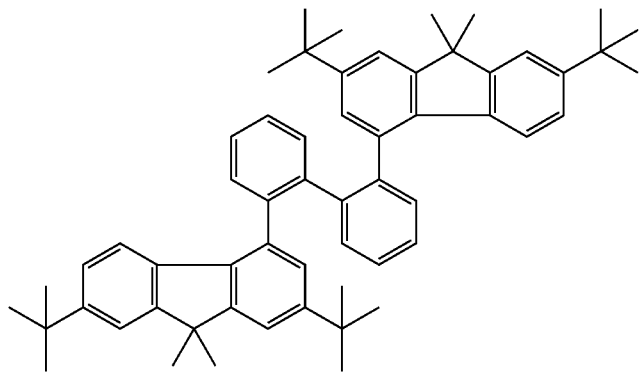
A-55
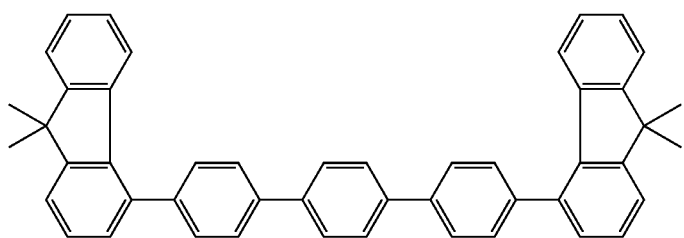

-continued
A-56
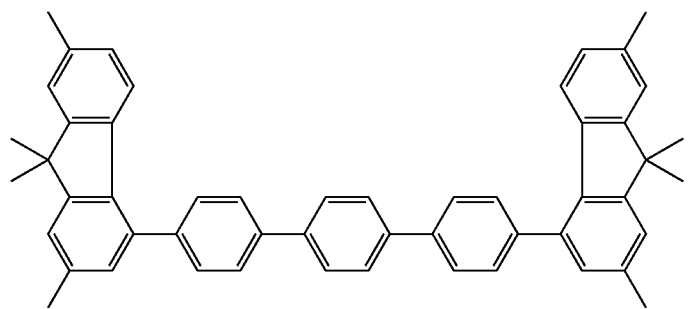
A-57
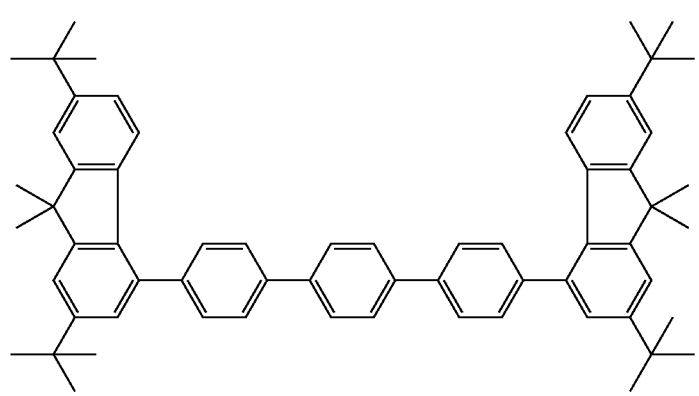
A-58
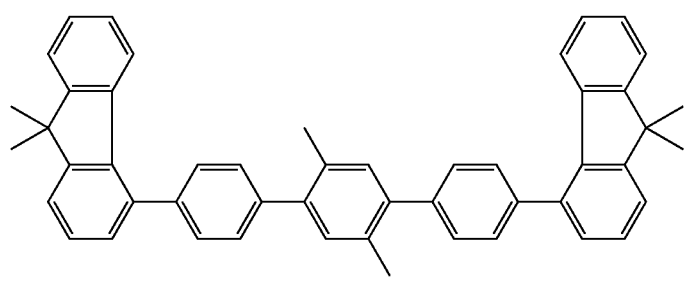
A-59
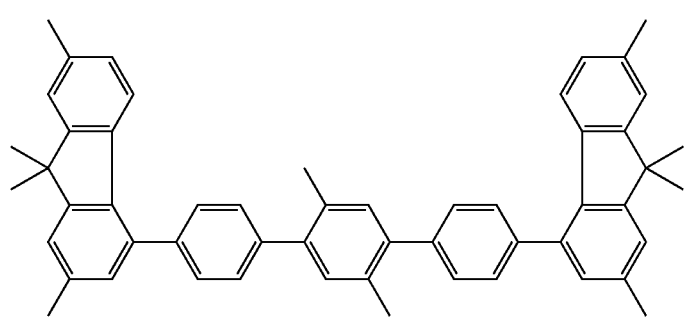
A-60
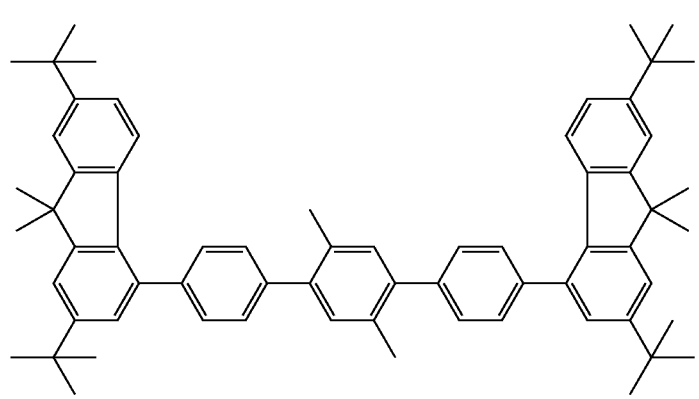

A-61
A-62
A-63
A-64
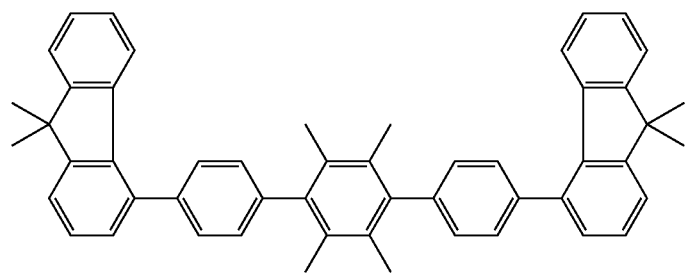

-continued
A-65
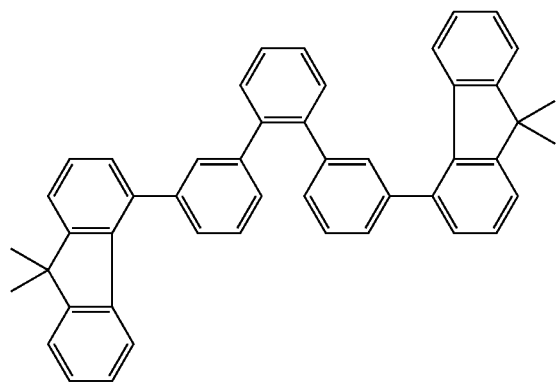
A-66
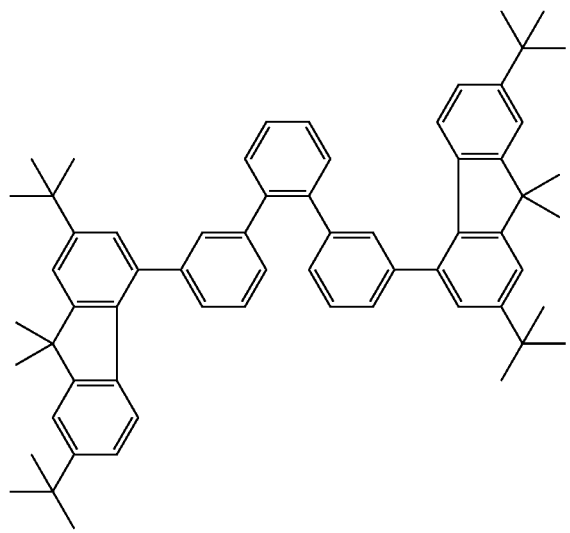
A-67
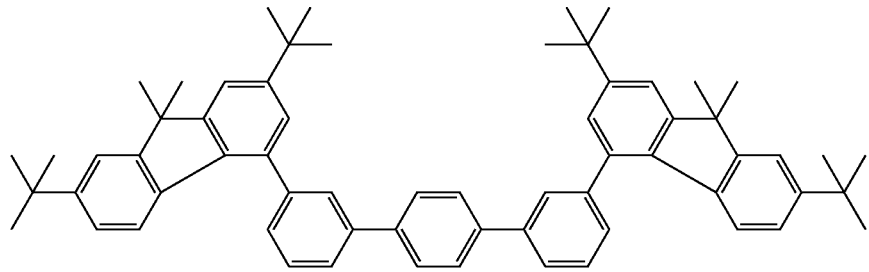
A-68
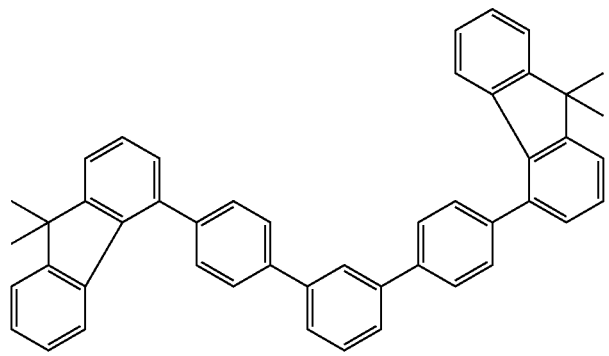
A-69
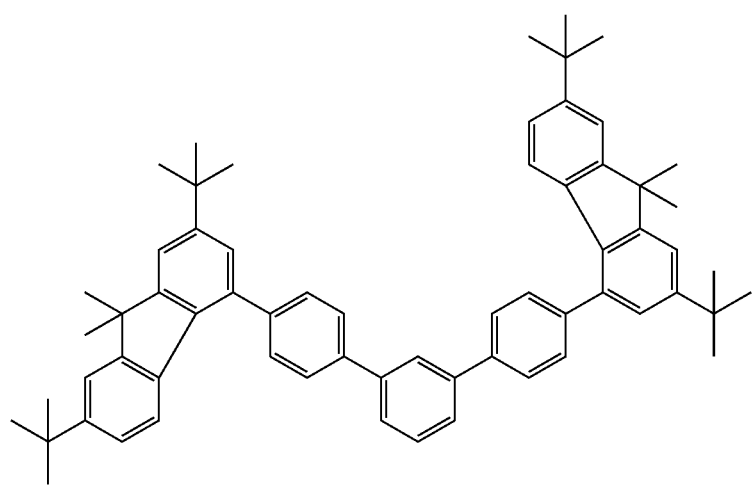

-continued
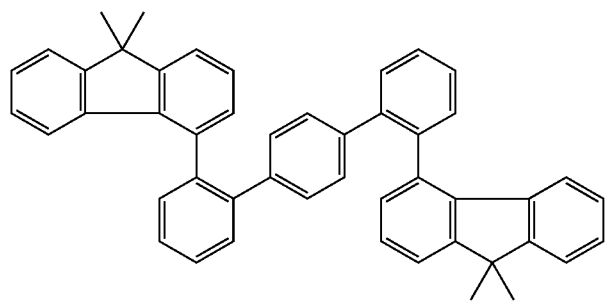
A-70
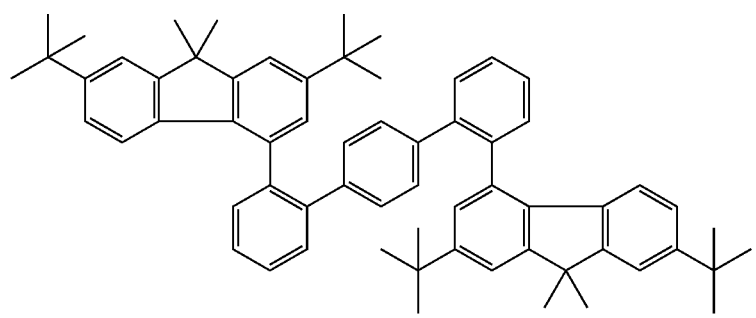
A-71
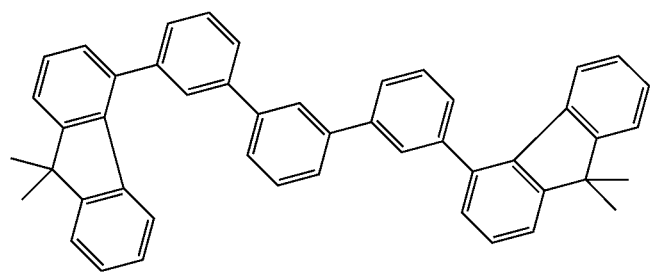
A-72
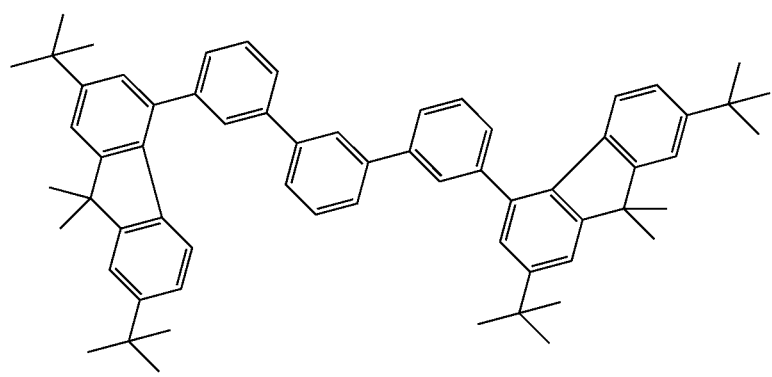
A-73
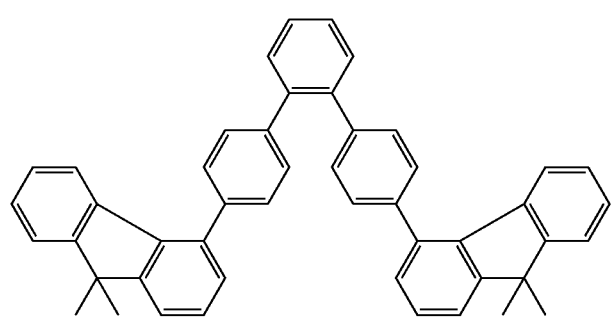
A-74

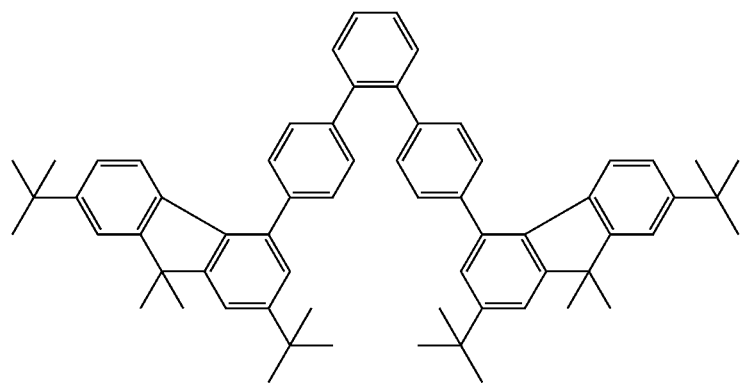
A-75
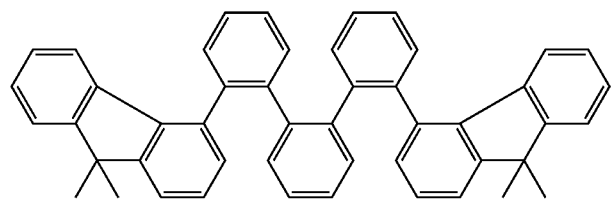
A-76
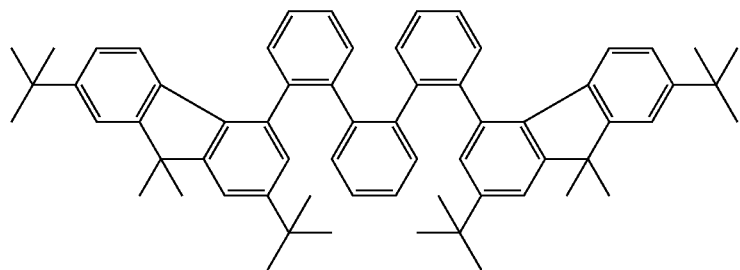
A-77
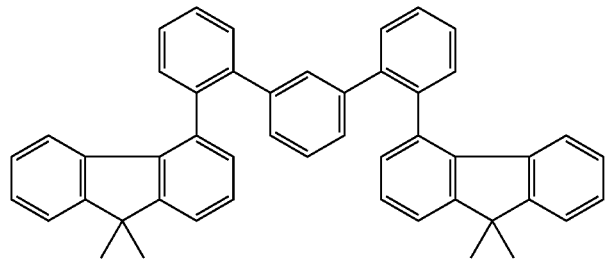
A-78
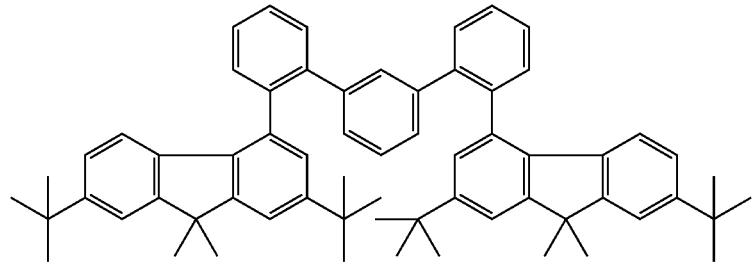
A-79

-continued
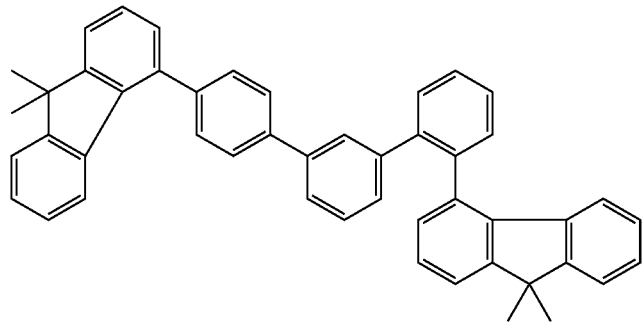
A-80
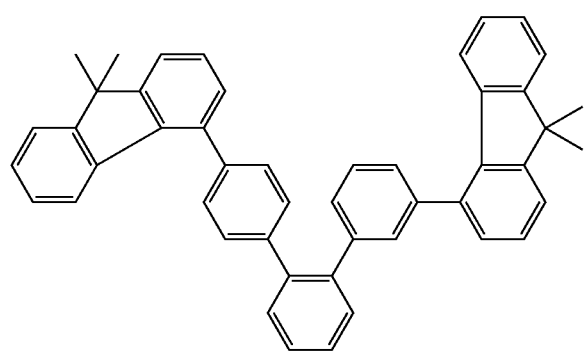
A-81
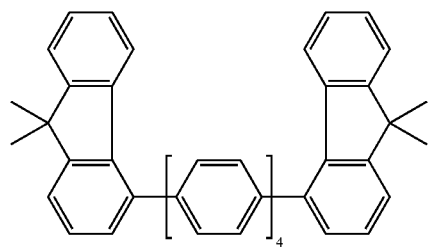
A-82
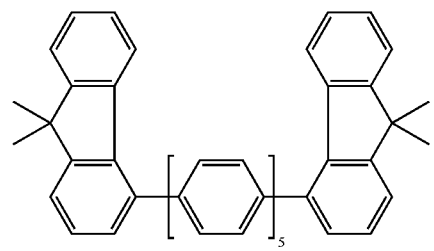
A-83
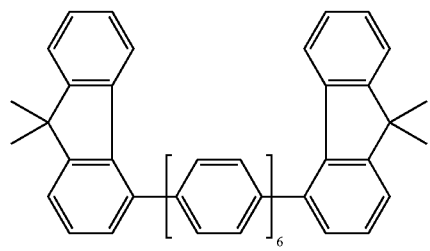
A-84
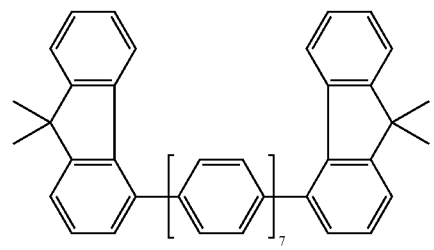
A-85
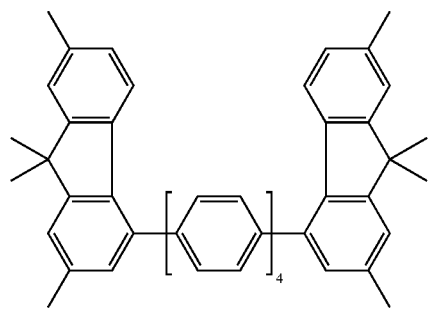
A-86
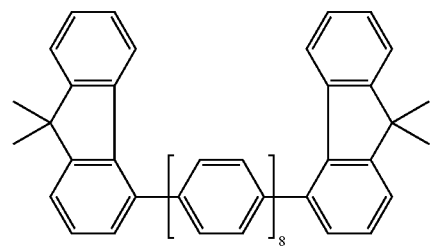
A-87

-continued
A-88
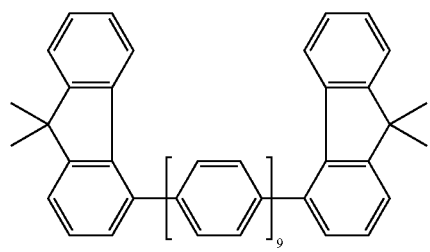
A-89
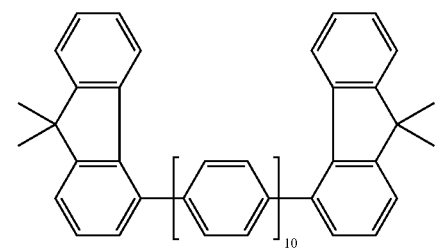
A-90
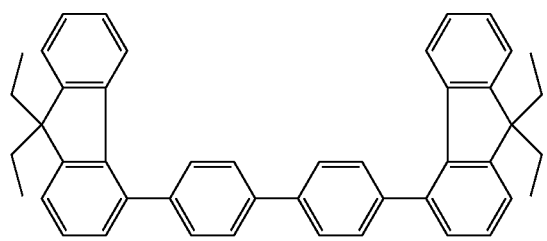
A-91
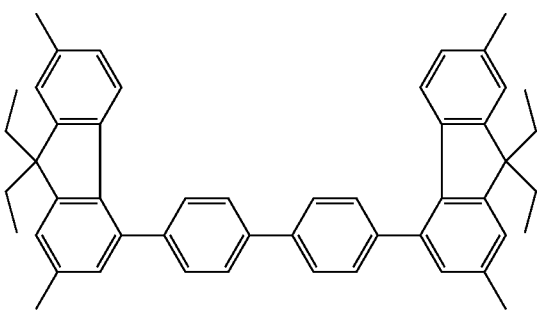
A-92
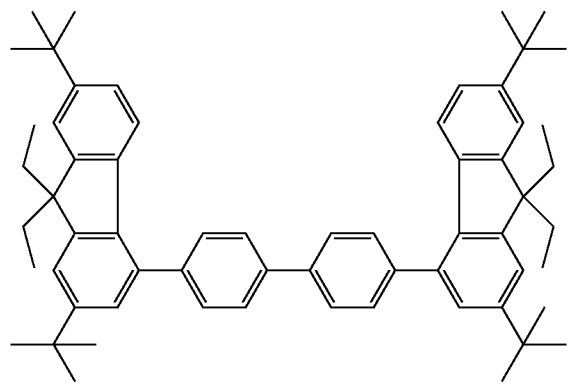
A-93
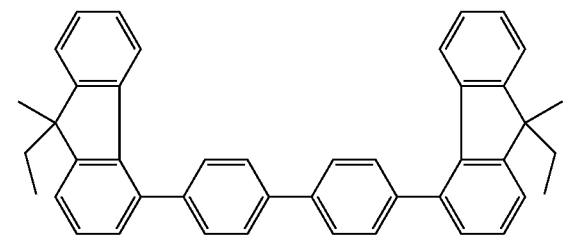
A-94
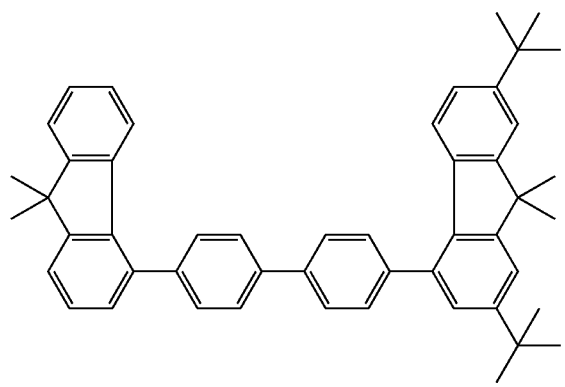
A-95
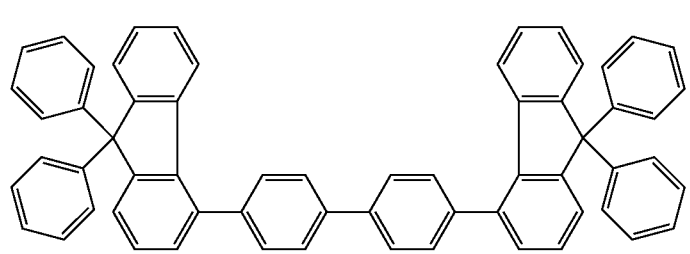

-continued
B-1
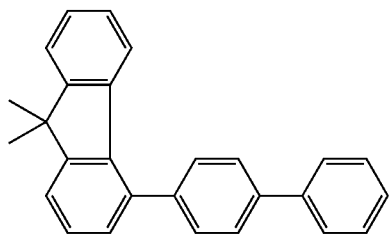
B-2
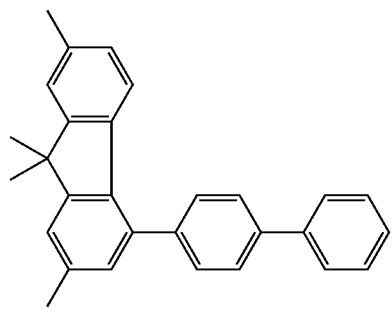
B-3
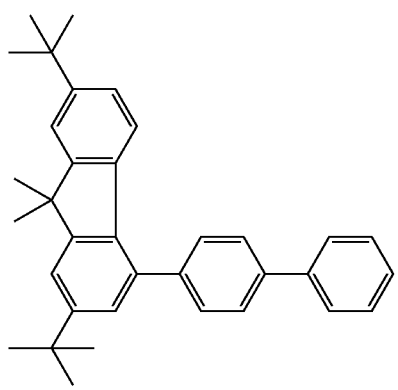
B-4
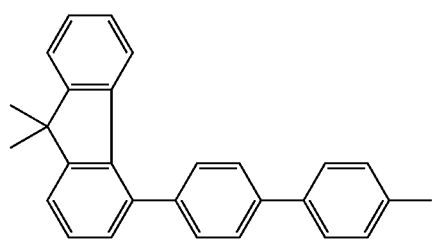
B-5
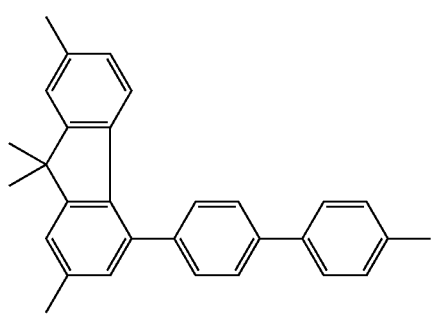
B-6
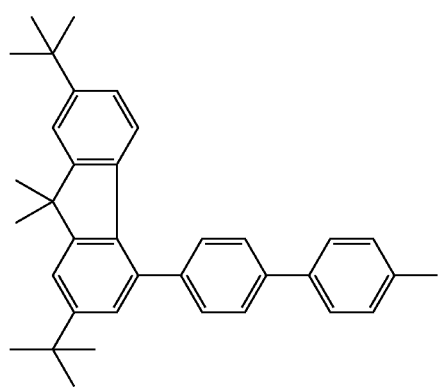
B-7
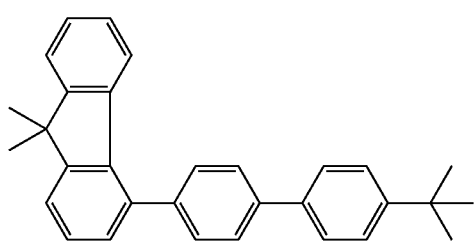
B-8
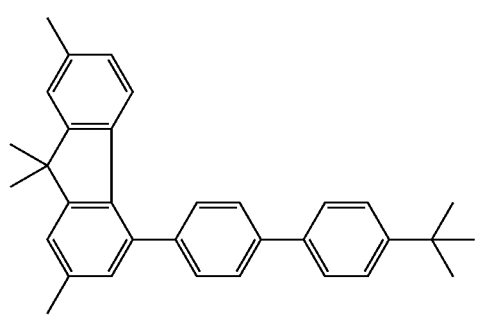

-continued
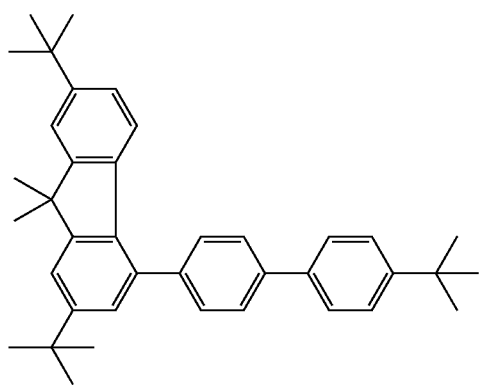
B-9
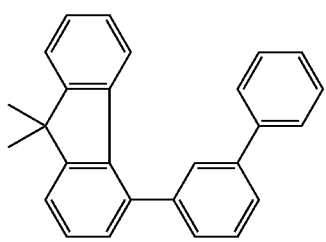
B-10
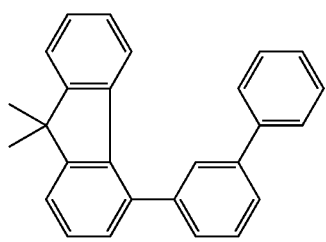
B-11
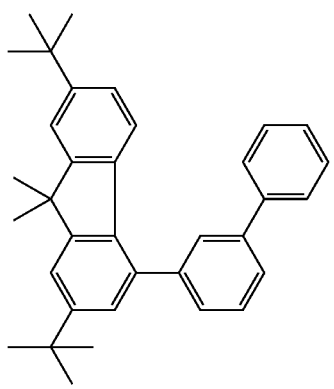
B-12
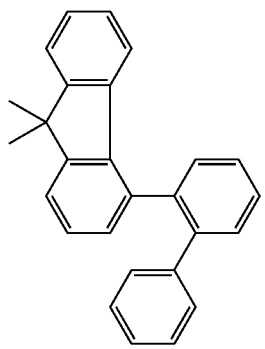
B-13
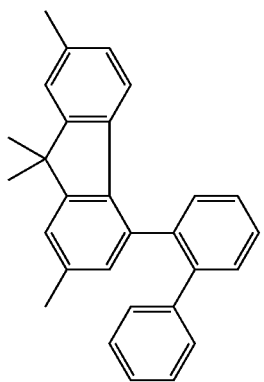
B-14
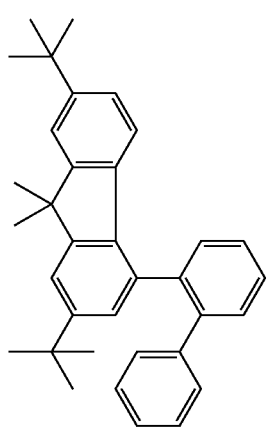
B-15
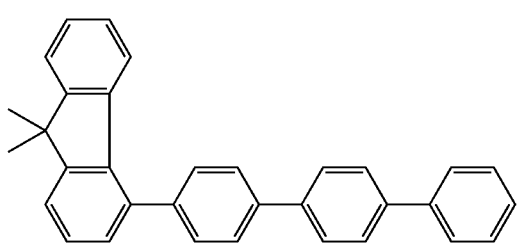
B-16

-continued
B-17
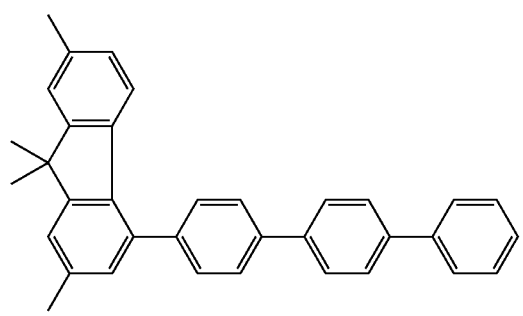
B-18
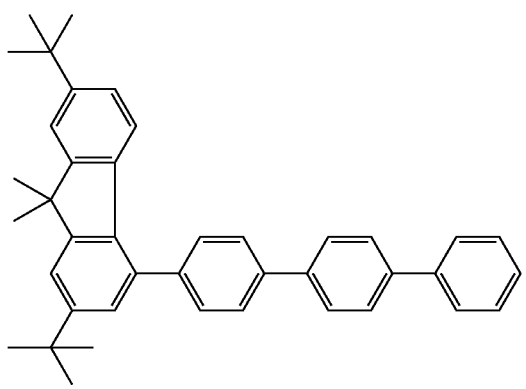
B-19
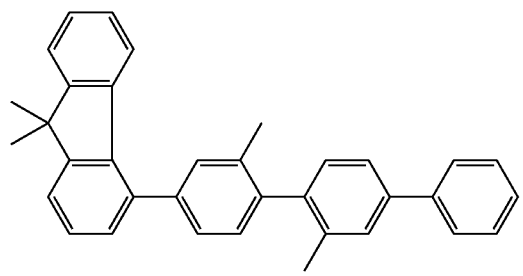
B-20
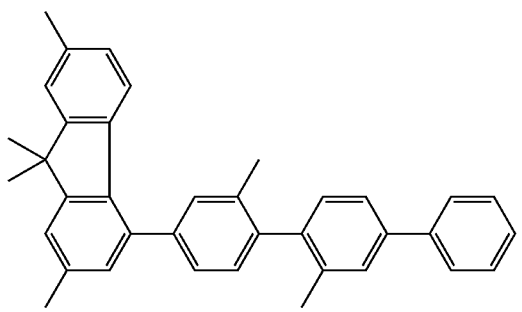
B-21
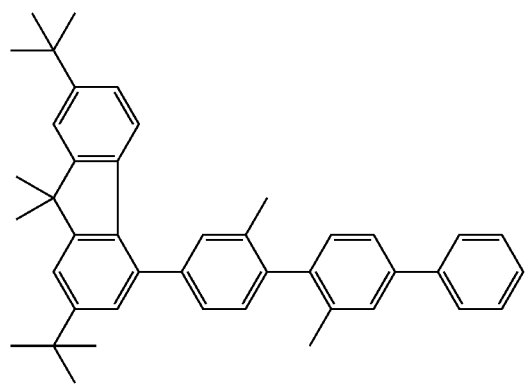
B-22
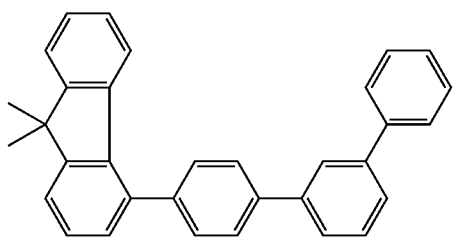
B-23
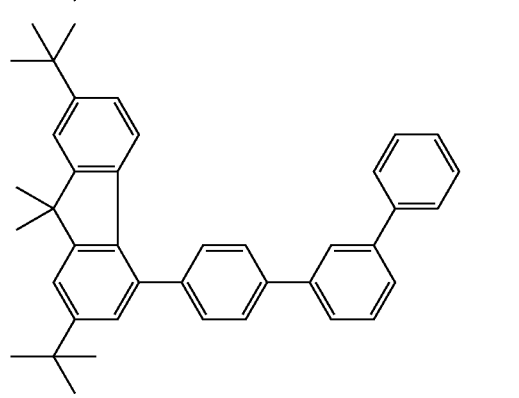
B-24
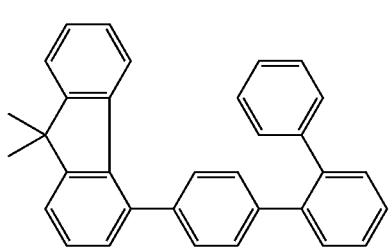

-continued
B-25
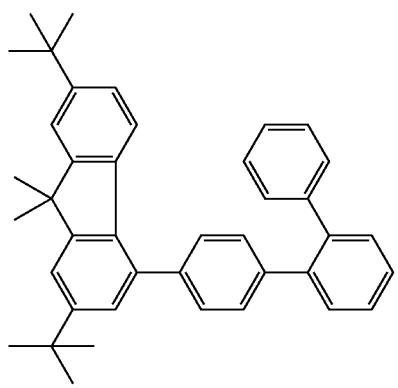
B-26
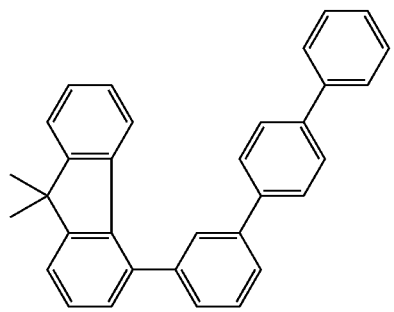
B-27
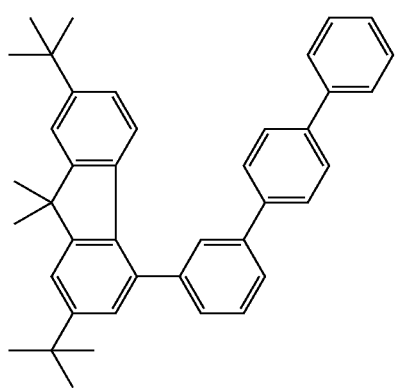
B-28
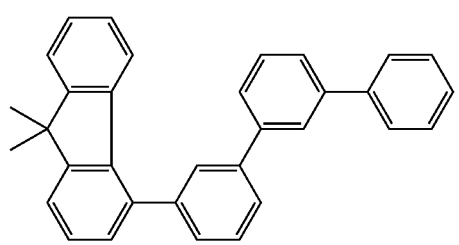
B-29
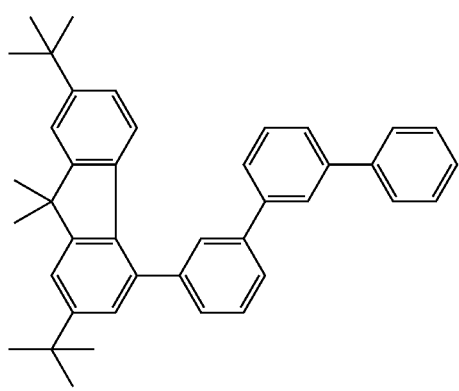
B-30
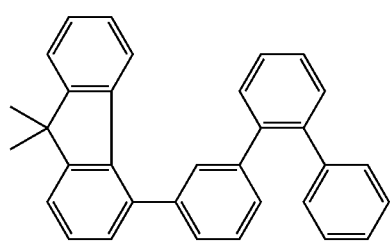
B-31
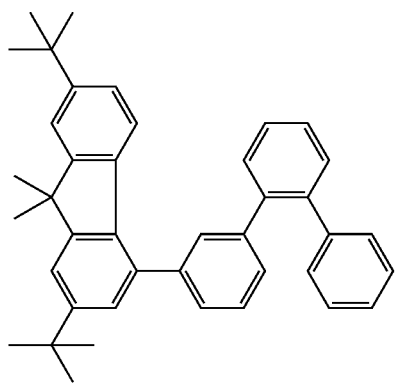
B-32
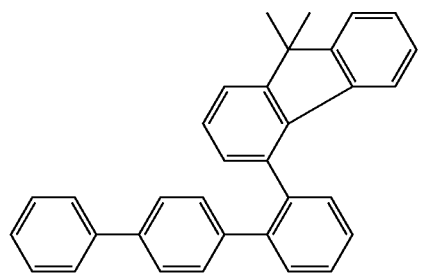

-continued
B-33
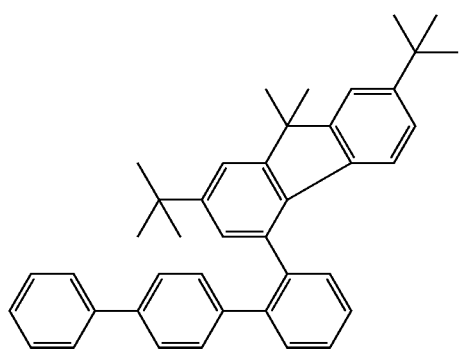
B-34
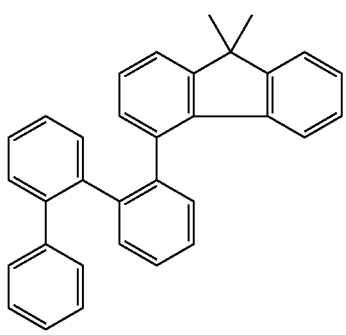
B-35
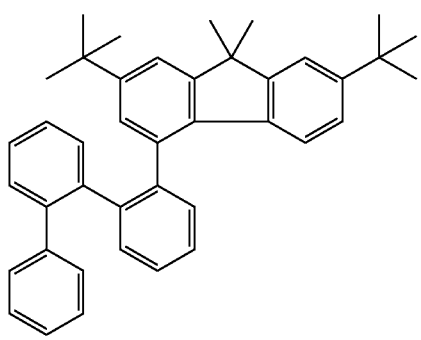
B-36
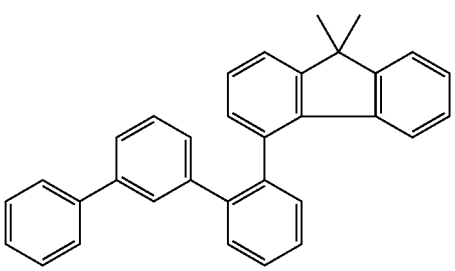
B-37
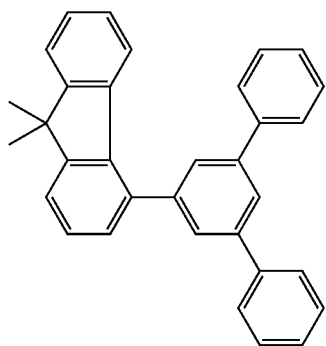
B-38
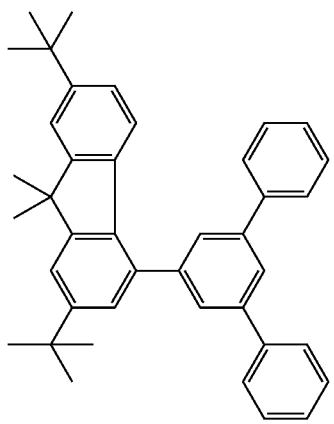
B-39
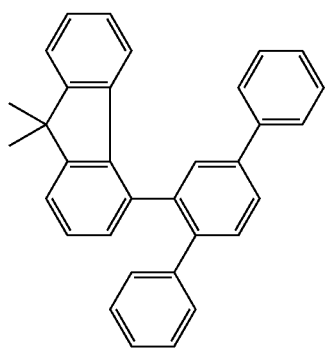
B-40
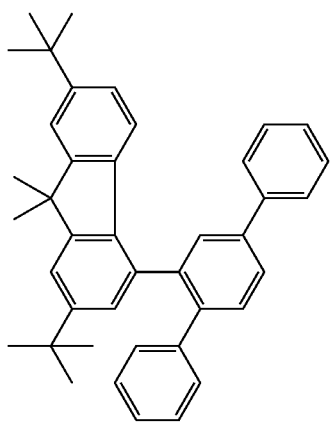

-continued
B-41
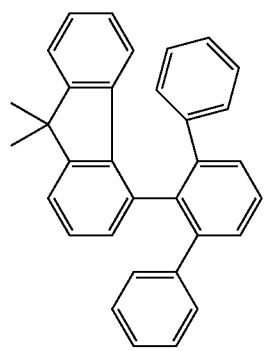
B-42
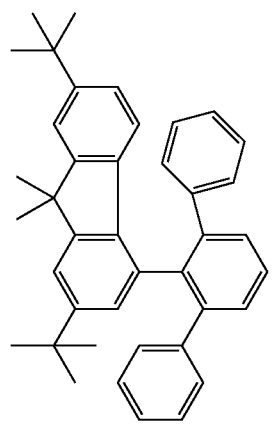
B-43
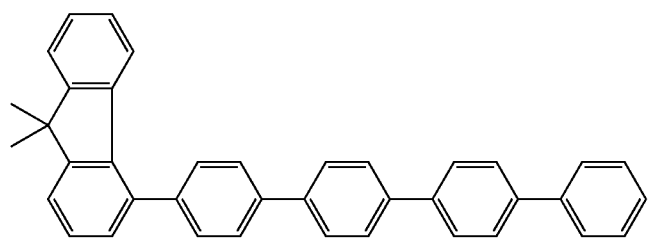
B-44
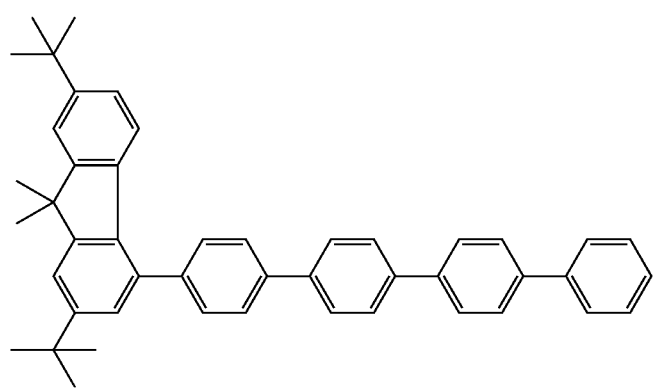
B-45
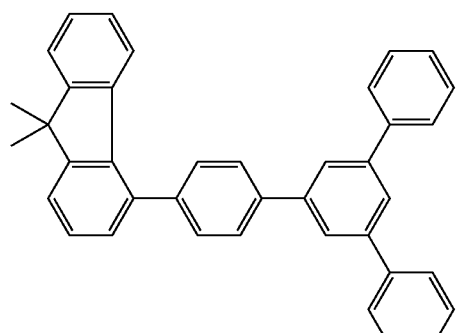
B-46
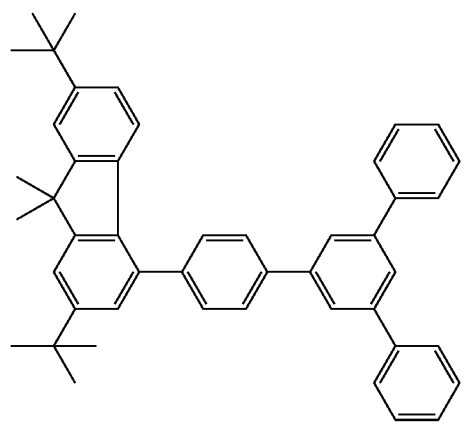

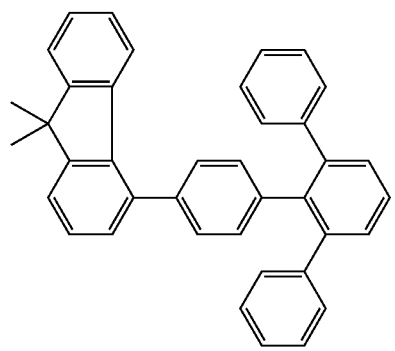

B-47

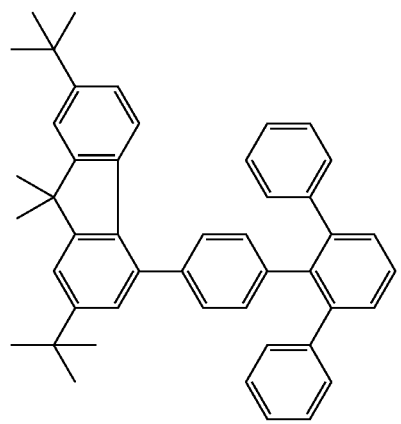

B-48

In addition, fluorescent materials and phosphorescent materials which are generally known can be used for a guest molecule when the fluorene derivative of the present invention is used as a host in a light-emitting layer. It is desirable to use metal complexes such as an Ir complex, a Pt complex, a Re complex, a Cu complex, a Eu complex, and a Rh complex which are known to emit phosphorescence to yield a light-emitting device with high efficiency. It is more desirable to use an Ir complex which is known to emit stronger phosphorescence. Further, the light-emitting layer can contain a plurality of phosphorescent materials to yield luminescence of multiple colors from the light-emitting layer and to support transfer of an exciton and a charge.

Specific structural formulae of the guest to be used in the present invention are described hereinbelow. Note that these structural formulae only show representative examples, and the present invention is not limited thereto.

-continued

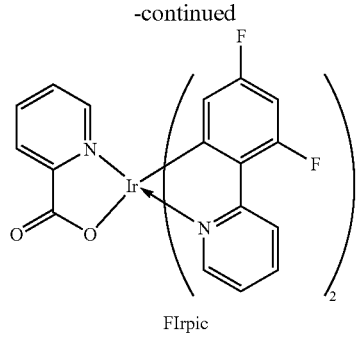

FIrpic

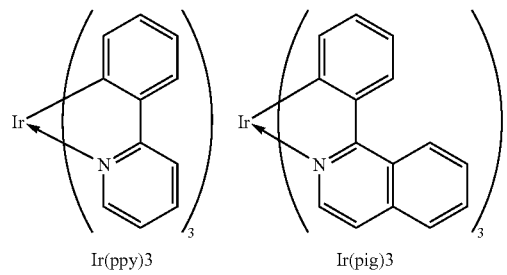

Ir(ppy)3   Ir(piq)3

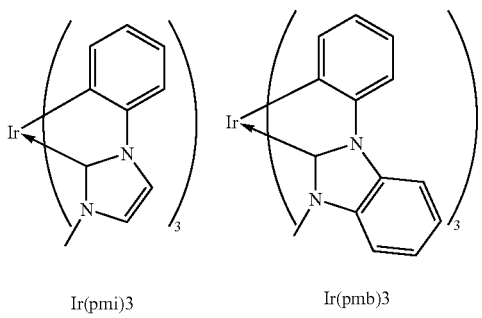

Ir(pmi)3   Ir(pmb)3

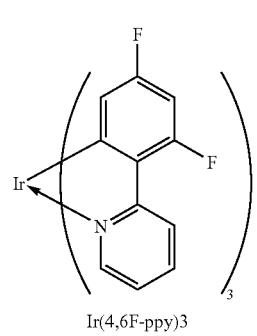

Ir(4,6F-ppy)3

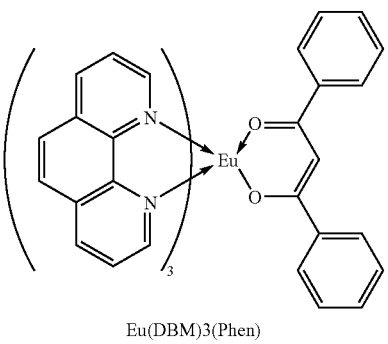

Eu(DBM)3(Phen)

-continued

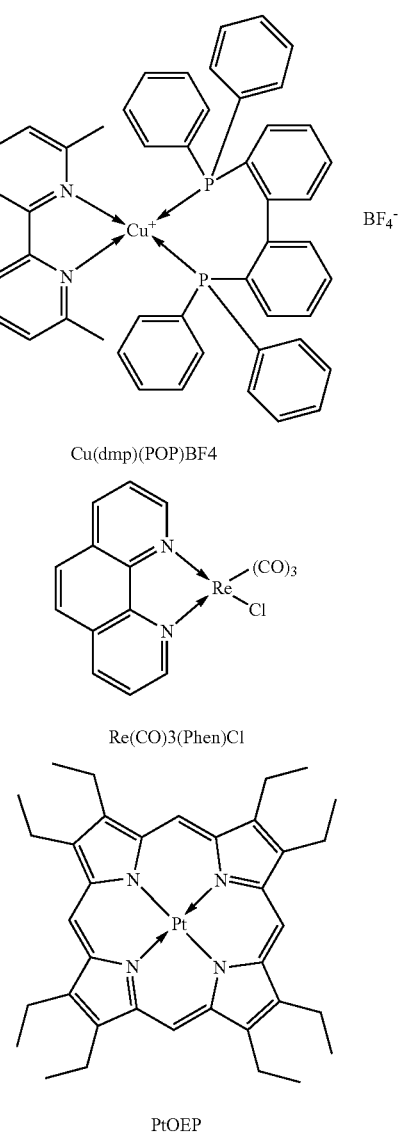

Cu(dtbp)(dmp)PF6

Cu(dmp)(POP)BF4

Re(CO)3(Phen)Cl

PtOEP

In a case where the fluorene derivative of the present invention is used as a host in a light-emitting layer, it is desirable that the light-emitting layer contains the host in a content of 50% by weight or more, and preferably 70% by weight or more and 99.9% by weight or less.

The organic layer containing the fluorene derivative of the present invention can be formed by film formation methods such as the vapor deposition method, the casting method, the coating method, the spin coating method, and the ink jet method.

Figure 2:
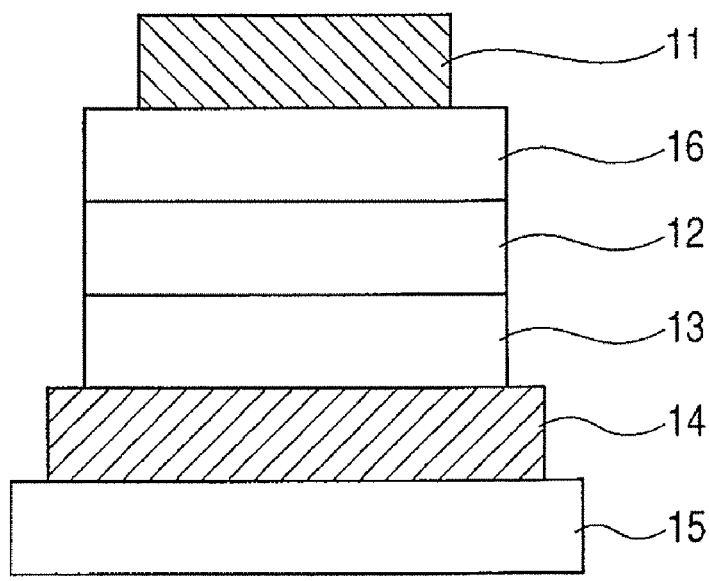
FIG. 2 shows another example of the organic EL device of the present invention.
Figure 3:
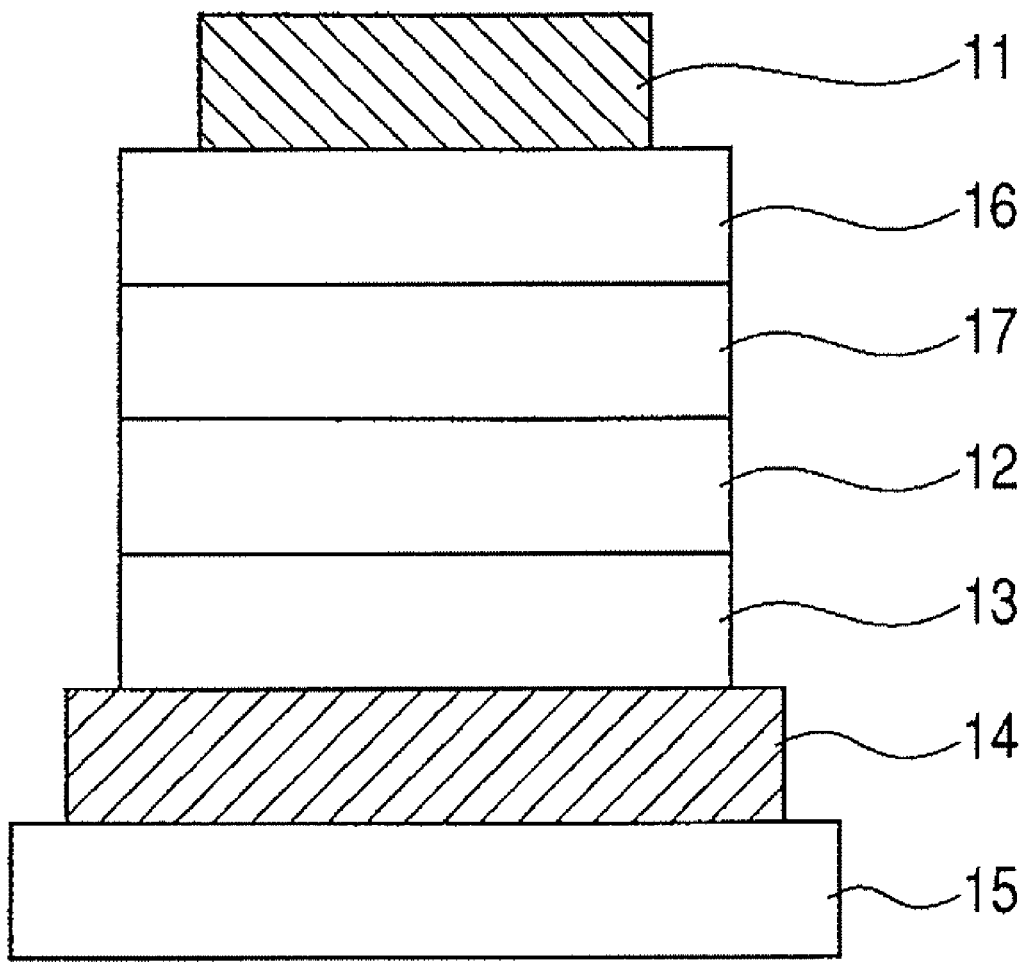
FIG. 3 shows another example of the organic EL device of the present invention.

Next, basic device constitution of the organic EL device of the present invention is shown in FIGS. 1 to 3.

First, reference numerals shown in the drawings are described as follows: a reference numeral 11 denotes a metal electrode; a reference numeral 12 denotes a light-emitting layer; a reference numeral 13 denotes a hole-transporting layer; a reference numeral 14 denotes a transparent electrode; a reference numeral 15 denotes a transparent substrate; a reference numeral 16 denotes an electron-transporting layer; and a reference numeral 17 denotes an exciton diffusion-prevention layer.

As shown in FIG. 1, an organic EL device is generally constituted by: a transparent substrate 15; a transparent electrode 14 having a thickness of 50 to 200 nm, which is arranged on the transparent substrate 15; multiple organic layers; and a metal electrode 11.

FIG. 1 shows an example in which the organic layers are a light-emitting layer 12 and a hole-transporting layer 13. ITO having a large work function or the like is used for the transparent electrode 14 to facilitate the injection of a hole from the transparent electrode 14 to the hole-transporting layer 13. A metal material having a small work function such as aluminum, magnesium, or an alloy using at least one of them is used for the metal electrode 11 to facilitate the injection of electrons to the organic layers.

The fluorene derivative of the present invention is used for the light-emitting layer 12. A material having electron-donating property such as a triphenyl diamine derivative typified by α-NPD can also be appropriately used for the hole-transporting layer 13.

The device having the above-mentioned constitution shows electrical rectifying property. When an electric field is applied in such a manner that the metal electrode 11 serves as a cathode and the transparent electrode 14 serves as an anode, an electron is injected from the metal electrode 11 to the light-emitting layer 12 and a hole is injected from the transparent electrode 14 thereto.

The injected hole and electron recombine in the light-emitting layer 12 to generate an exciton, thereby emitting light. At this time, the hole-transporting layer 13 serves as an electron-blocking layer, and recombination efficiency at an interface between the light-emitting layer 12 and the hole-transporting layer 13 increases, whereby emission efficiency increases.

In FIG. 2, an electron-transporting layer 16 is interposed between the metal electrode 11 and the light-emitting layer 12 shown in FIG. 1. In this case, emission efficiency is increased by separating a light emitting function and electron- and hole-transporting functions to provide a carrier blocking structure having improved effectiveness. An oxadiazole derivative or the like can be used for the electron-transporting layer 16.

As shown in FIG. 3, a four-layer structure including the hole-transporting layer 13, the light-emitting layer 12, an exciton diffusion-prevention layer 17, the electron-transporting layer 16, and the metal electrode 11 from the side of the transparent electrode 14 as an anode is also desirable.

EXAMPLES

Hereinafter, the present invention will be described specifically by way of examples. However, the present invention is not limited to these examples.

Example 1 (Synthesis of Exemplified Compound No. A-24-1)

Exemplified Compound No. A-24-1 was synthesized by a reaction as described below.

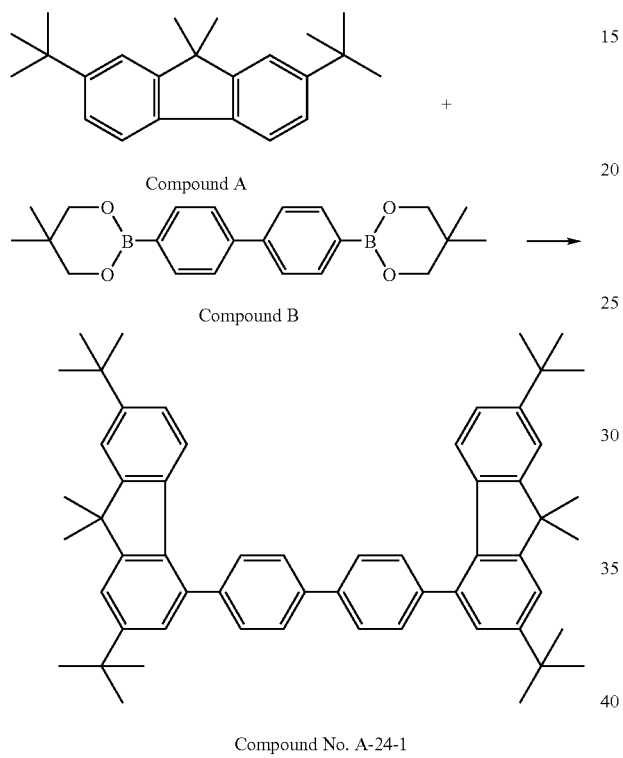

Compound No. A-24-1

2.04 g (5.29 mmole) of Compound A, 1.00 g (2.65 mmole) of Compound B, 0.26 g of Pd(PPh$_3$)$_4$, 20 ml of toluene, 10 ml of ethanol, and 20 ml of a 2 M aqueous cesium carbonate solution were added to a 100-ml flask, and the whole was stirred at 80° C. for 8 hours under nitrogen atmosphere. After completion of the reaction, the reaction solution was subjected to extraction with toluene. An organic layer was washed with water and dried with magnesium sulfate, followed by drying under reduced pressure. The resultant product was purified by silica gel column chromatography using a toluene eluent, and then subjected to recrystallization with toluene/ethanol. A crystal thus obtained was dried in vacuum and then subjected to sublimation and purification to yield 1.45 g (72.0% yield) of Exemplified Compound No. A-24-1.

Exemplified Compound No. A-24-1 was confirmed to have M+ of 762.5 by matrix-assisted laser desorption ionization-time of flight mass spectrometry (MALDI-TOF MS).

In addition, the structure of the compound was confirmed by NMR measurement.

1H NMR (CDCl$_3$, 500 MHz) δ(ppm): 7.86 (d, 4H, J=7.9 Hz), 7.64 (d, 4H, J=7.9 Hz), 7.46 (d, 2H, J=1.9 Hz), 7.42 (d, 2H, J=1.9 Hz), 7.24 (d, 2H, J=1.9 Hz), 7.10 (dd, 2H, J=8.2, 1.9 Hz), 7.01 (d, 2H, J=8.2 Hz), 1.54 (s, 12H), 1.42 (s, 18H), 1.33 (s, 18H)

Example 2

In this example, a device having three (3) organic layers as described below was used as a device constitution. ITO was patterned onto a glass substrate to have a thickness of 100 nm. The following organic layers and electrode layers were continuously formed onto the ITO substrate through vacuum evaporation according to resistance heating in a vacuum chamber at 10$^{-5}$ Pa so that opposing electrodes each have an area of 3 mm$^2$.

Hole-transporting layer (50 nm): α-NPD
Light-emitting layer (30 m): Exemplified Compound No. A-24-1:Ir(ppy)$_3$ (weight ratio of 8%)
Electron-transporting layer (30 nm): Bphen (manufactured by Dojindo Laboratories)
Metal electrode layer 1 (1 nm): KF
Metal electrode layer 2 (150 nm): Al Properties of the EL device were determined as follows: current/voltage characteristics thereof were measured with a micro ammeter 4140B manufactured by Hewlett-Packard Development Company; and luminance was measured with BM7 manufactured by Topcon Corporation. The efficiency of the device of this example was 52.0 cd/A. In addition, the device was subjected to continuous energization, and as a result, stable green phosphorescence was able to be observed even after the device was energized continuously for 100 hours.

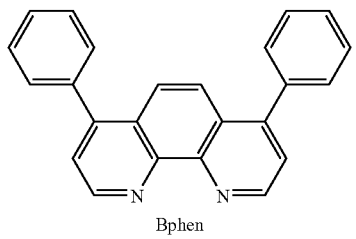

Bphen

Example 3

A device was prepared in the same manner as in Example 2 except that Ir(4,6-Fppy)$_3$ (weight ratio of 8%) was used instead of Ir(ppy)$_3$ (weight ratio of 8%) used in Example 2. The efficiency of the device of this example was 5.2 cd/A. In addition, the device was subjected to continuous energization, and as a result, stable green phosphorescence was able to be observed even after the device was energized continuously for 100 hours.

As described above, the organic EL device of the present invention, which was obtained by using as a host in a light-emitting layer the fluorene derivative represented by the general formula (I) was excellent because the organic EL device not only had high efficiency but retained high luminance for a long period of time.

The present invention uses as a host in a light-emitting layer the fluorene derivative having the particular structure, so the present invention can be utilized for an organic EL device which can emit light with high efficiency and retain high luminance for a long period of time.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-099895, filed Mar. 31, 2006, which is hereby incorporated by reference herein in its entirety.

What is claimed is:

1. A fluorene derivative represented by the following formula:

A-24-1

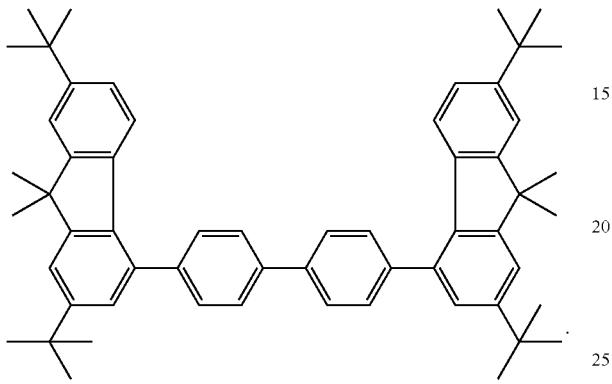

2. A fluorene derivative which is represented by the general formula (I):

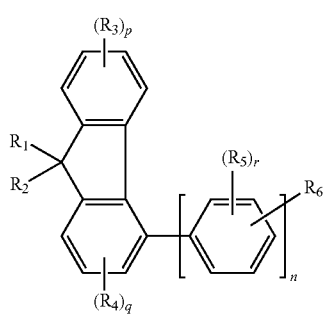

[I]

wherein, $R_1$ and $R_2$ each represent a hydrogen atom, an alkyl group, a substituted or unsubstituted aralkyl group, a substituted or unsubstituted aryl group, or a substituted or unsubstituted heterocyclic group, provided that $R_1$ and $R_2$ may be identical to or different from each other;

$R_3$ and $R_4$ each represent a linear, branched, or cyclic alkyl group wherein at least one methylene group in the alkyl group may be substituted by —O—, —S—, —CO—, —CO—O—, —O—CO—, —CH=CH—, —C≡C—, or an arylene group which may have a substituent, and a hydrogen atom in the alkyl group may be substituted by a fluorine atom;

p represents an integer of 0 to 1, and q represents an integer of 0 to 1;

$R_5$ represents a linear, branched, or cyclic alkyl group wherein at least one methylene group in the alkyl group may be substituted by —O—, —S—, —CO—, —CO—O—, —O—CO—, —CH=CH—, —C≡C—, or an arylene group which may have a substituent, and a hydrogen atom in the alkyl group may be substituted by a fluorine atom; a halogen atom; an unsubstituted aryl group, provided that, when $R_5$ is present in plurality, $R_5$'s may be identical to or different from each other;

r represents an integer of 0 to 4;

when the phenylene group is present in plurality, the substituents $R_5$'s of phenylene groups may be identical to or different from each other, and the substituents $R_6$'s of phenylene groups may be identical to or different from each other;

n represents an integer of 1 to 10; and $R_6$ is represented by the general formula (II):

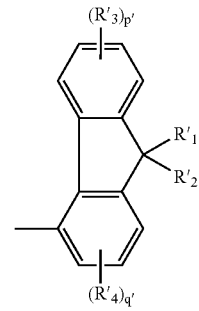

[II]

wherein, $R'_1$ and $R'_2$ each represent a hydrogen atom, an alkyl group, a substituted or unsubstituted aralkyl group, a substituted or unsubstituted aryl group, or a substituted or unsubstituted heterocyclic group, provided that $R'_1$ and $R'_2$ may be identical to or different from each other;

$R'_3$ and $R'_4$ each represent a linear, branched, or cyclic alkyl group wherein at least one methylene group in the alkyl group may be substituted by —O—, —S—, —CO—, —CO—O—, —O—CO—, —CH=CH—, —C≡C—, or an arylene group which may have a substituent, and a hydrogen atom in the alkyl group may be substituted by a fluorine atom; a substituted or unsubstituted aryl group; or a halogen atom, provided that, when $R'_3$ and $R'_4$ are each present in plurality, $R'_3$'s may be identical to or different from each other, and $R'_4$'s may be identical to or different from each other; and p' represents an integer of 0 to 4, and q' represents an integer of 0 to 3.

3. An organic electroluminescence device comprising:

a pair of electrodes; and an organic compound layer which is interposed between the pair of the electrodes, wherein the organic compound layer contains a fluorene derivative which is represented by the general formula (I):

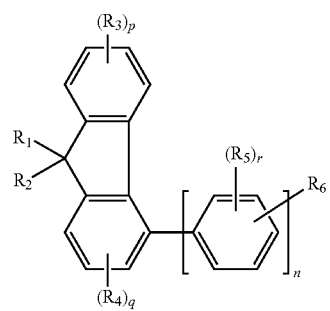

[I]

wherein, $R_1$ and $R_2$ each represent a hydrogen atom, an alkyl group, a substituted or unsubstituted aralkyl group, a substituted or unsubstituted aryl group, or a substituted or unsubstituted heterocyclic group, provided that $R_1$ and $R_2$ may be identical to or different from each other;

$R_3$ and $R_4$ each represent a linear, branched, or cyclic alkyl group wherein at least one methylene group in the alkyl group may be substituted by —O—, —S—, —CO—, —CO—O—, —O—CO—, —CH=CH—, —C≡C—, or an arylene group which may have a substituent, and a hydrogen atom in the alkyl group may be substituted by a fluorine atom;

p represents an integer of 0 to 1, and q represents an integer of 0 to 1;

$R_5$ represents a linear, branched, or cyclic alkyl group wherein at least one methylene group in the alkyl group may be substituted by —O—, —S—, —CO—, —CO—O—, —O—CO—, —CH=CH—, —C≡C—, or an arylene group which may have a substituent, and a hydrogen atom in the alkyl group may be substituted by a fluorine atom; a halogen atom; an unsubstituted aryl group, provided that, when $R_5$ is present in plurality, $R_5$'s may be identical to or different from each other;

r represents an integer of 0 to 4;

when the phenylene group is present in plurality, the substituents $R_5$'s of phenylene groups may be identical to or different from each other, and the substituents $R_6$'s of phenylene groups may be identical to or different from each other;

n represents an integer of 1 to 10; and $R_6$ is represented by the general formula (II):

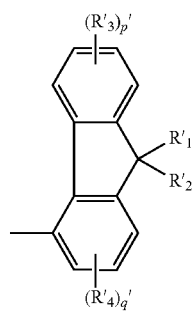

[II]

wherein, $R'_1$ and $R'_2$ each represent a hydrogen atom, an alkyl group, a substituted or unsubstituted aralkyl group, a substituted or unsubstituted aryl group, or a substituted or unsubstituted heterocyclic group, provided that $R'_1$ and $R'_2$ may be identical to or different from each other;

$R'_3$ and $R'_4$ each represent a linear, branched, or cyclic alkyl group wherein at least one methylene group in the alkyl group may be substituted by —O—, —S—, —CO—, —CO—O—, —O—CO—, —CH=CH—, —C≡C—, or an arylene group which may have a substituent, and a hydrogen atom in the alkyl group may be substituted by a fluorine atom; a substituted or unsubstituted aryl group; or a halogen atom, provided that, when $R'_3$ and $R'_4$ are each present in plurality, $R'_3$'s may be identical to or different from each other, and $R'_4$'s may be identical to or different from each other; and p' represents an integer of 0 to 4, and q' represents an integer of 0 to 3.

4. A display apparatus comprising the organic electroluminescence device according to claim 3.

5. An organic electroluminescence device comprising:

a pair of electrodes; and an organic compound layer which is interposed between the pair of the electrodes, wherein the organic compound layer contains a fluorene derivative which is represented by the general formula (I):

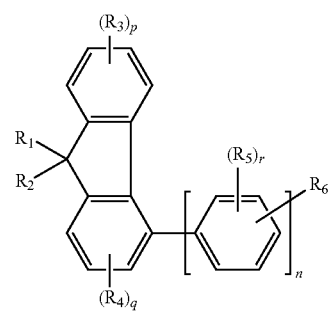

[I]

wherein, $R_1$ and $R_2$ each represent a hydrogen atom, an alkyl group, a substituted or unsubstituted aralkyl group, a substituted or unsubstituted aryl group, or a substituted or unsubstituted heterocyclic group, provided that $R_1$ and $R_2$ may be identical to or different from each other;

$R_3$ and $R_4$ each represent a linear, branched, or cyclic alkyl group wherein at least one methylene group in the alkyl group may be substituted by —O—, —S—, —CO—, —CO—O—, —O—CO—, —CH=CH—, —C≡C—, or an arylene group which may have a substituent, and a hydrogen atom in the alkyl group may be substituted by a fluorine atom;

p represents an integer of 0 to 1, and q represents an integer of 0 to 1;

$R_5$ represents a linear, branched, or cyclic alkyl group wherein at least one methylene group in the alkyl group may be substituted by —O—, —S—, —CO—, —CO—O—, —O—CO—, —CH=CH—, —C≡C—, or an arylene group which may have a substituent, and a hydrogen atom in the alkyl group may be substituted by a fluorine atom; a halogen atom; an unsubstituted aryl group, provided that, when $R_5$ is present in plurality, $R_5$'s may be identical to or different from each other;

r represents an integer of 0 to 4;

when the phenylene group is present in plurality, the substituents $R_5$'s of phenylene groups may be identical to or different from each other, and the substituents $R_6$'s of phenylene groups may be identical to or different from each other;

n represents an integer of 1 to 10; and $R_6$ is a hydrogen atom, or a linear, branched, or cyclic alkyl group.

6. A display apparatus comprising the organic electroluminescence device according to claim 5.

7. An organic electroluminescence device comprising:

a pair of electrodes; and an organic compound layer which is interposed between the pair of the electrodes, wherein the organic compound layer contains a fluorene derivative represented by the following formula:

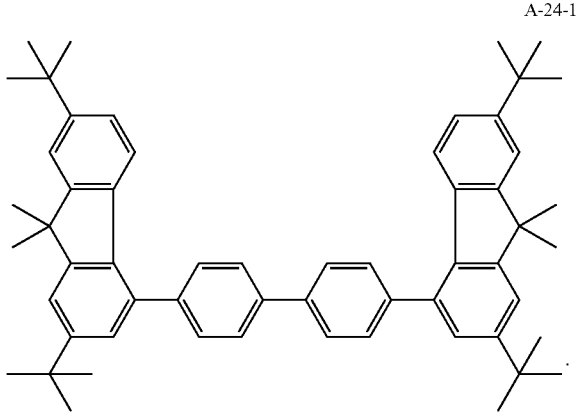

A-24-1

8. A display apparatus comprising the organic electroluminescence device according to claim 7.

9. An organic electroluminescence device comprising:
a pair of electrodes; and
an organic compound layer which is interposed between the pair of the electrodes,
wherein the organic compound layer contains a fluorene derivative which is represented by the general formula (I):

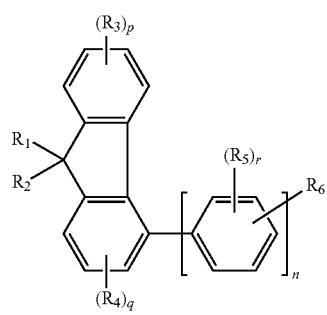

[I]

wherein, $R_1$ and $R_2$ each represent a hydrogen atom, an alkyl group, a substituted or unsubstituted aralkyl group, a substituted or unsubstituted aryl group, or a substituted or unsubstituted heterocyclic group, provided that $R_1$ and $R_2$ may be identical to or different from each other;

$R_3$ and $R_4$ each represent a linear, branched, or cyclic alkyl group wherein at least one methylene group in the alkyl group may be substituted by —O—, —S—, —CO—, —CO—O—, —O—CO—, —CH=CH—, —C≡C—, or an arylene group which may have a substituent, and a hydrogen atom in the alkyl group may be substituted by a fluorine atom;

p represents an integer of 0 to 1, and q represents an integer of 0 to 1;

$R_5$ represents a linear, branched, or cyclic alkyl group wherein at least one methylene group in the alkyl group may be substituted by —O—, —S—, —CO—, —CO—O—, —O—CO—, —CH=CH—, —C≡C—, or an arylene group which may have a substituent, and a hydrogen atom in the alkyl group may be substituted by a fluorine atom; a halogen atom; an unsubstituted aryl group, provided that, when $R_5$ is present in plurality, $R_5$'s may be identical to or different from each other;

r represents an integer of 0 to 4;

when the phenylene group is present in plurality, the substituents $R_5$'s of phenylene groups may be identical to or different from each other, and the substituents $R_6$'s of phenylene groups may be identical to or different from each other;

n represents an integer of 1 to 10; and $R_6$ represents a hydrogen atom, an unsubstituted aryl group, or a linear, branched, or cyclic alkyl group.

10. An organic electroluminescence device according to claim 9, wherein the organic compound layer is a light-emitting layer.

11. An organic electroluminescence device according to claim 10, wherein the light-emitting layer at least comprises two kinds of compounds which are a host and a guest, respectively.

12. An organic electroluminescence device according to claim 11, wherein the host is the fluorene derivative.

13. An organic electroluminescence device according to claim 11, wherein the guest is a green phosphorescent material.

14. An organic electroluminescence device according to claim 13, wherein the phosphorescent material is a metal coordination compound.

15. An organic electroluminescence device according to claim 14, wherein the metal coordination compound is an iridium coordination compound.

16. A display apparatus comprising the organic electroluminescence device according to claim 9.

* * * * *